US009655863B2

(12) United States Patent
Smith et al.

(10) Patent No.: US 9,655,863 B2
(45) Date of Patent: *May 23, 2017

(54) MATRIX AND LAYER COMPOSITIONS FOR PROTECTION OF BIOACTIVES

(71) Applicant: Novus International Inc., St. Charles, MO (US)

(72) Inventors: Houston Stephen Smith, St. Charles, MO (US); Matthew J. Fischer, St. Charles, MO (US); Graciela B. Arhancet, St. Charles, MO (US); Rangarani Karnati, St. Charles, MO (US); John A. Hume, St. Charles, MO (US); Xiaojun Wang, St. Charles, MO (US)

(73) Assignee: Novus International, Inc., St. Charles, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/133,448

(22) Filed: Apr. 20, 2016

(65) Prior Publication Data

US 2016/0228391 A1    Aug. 11, 2016

Related U.S. Application Data

(63) Continuation of application No. 14/413,540, filed as application No. PCT/US2013/050051 on Jul. 11, 2013.

(60) Provisional application No. 61/670,817, filed on Jul. 12, 2012.

(51) Int. Cl.
| A61K 47/00 | (2006.01) |
| A61K 9/50 | (2006.01) |
| A61K 31/19 | (2006.01) |
| A61K 9/16 | (2006.01) |
| A61K 31/131 | (2006.01) |
| A61K 31/198 | (2006.01) |
| A23K 40/35 | (2016.01) |
| A23K 50/10 | (2016.01) |
| A23L 33/10 | (2016.01) |
| A23K 40/30 | (2016.01) |
| A23K 20/00 | (2016.01) |
| A23L 1/00 | (2006.01) |
| A23L 1/30 | (2006.01) |
| A23L 33/12 | (2016.01) |
| A23L 29/20 | (2016.01) |
| A23L 29/269 | (2016.01) |

(52) U.S. Cl.
CPC ............ *A61K 9/5042* (2013.01); *A23K 20/00* (2016.05); *A23K 40/30* (2016.05); *A23K 40/35* (2016.05); *A23K 50/10* (2016.05); *A23L 1/0047* (2013.01); *A23L 1/30* (2013.01); *A23L 29/20* (2016.08); *A23L 29/272* (2016.08); *A23L 33/10* (2016.08); *A23L 33/12* (2016.08); *A61K 9/1617* (2013.01); *A61K 9/1652* (2013.01); *A61K 9/501* (2013.01); *A61K 9/5015* (2013.01); *A61K 9/5026* (2013.01); *A61K 9/5031* (2013.01); *A61K 31/131* (2013.01); *A61K 31/19* (2013.01); *A61K 31/198* (2013.01); *A23V 2002/00* (2013.01); *A61K 9/5078* (2013.01)

(58) Field of Classification Search
None
See application file for complete search history.

(56) References Cited

U.S. PATENT DOCUMENTS

| 2,787,595 A | 4/1957 | Webb |
| 3,272,860 A | 9/1966 | Nufer |
| 3,288,859 A | 11/1966 | Lyness |
| 3,290,254 A | 12/1966 | Anderson |
| 3,329,617 A | 7/1967 | von Doering |
| 3,761,518 A | 9/1973 | Haglid |
| 3,773,927 A | 11/1973 | Cummins |
| 4,033,938 A | 7/1977 | Augurt |
| 4,095,029 A | 6/1978 | Fields |
| 4,235,942 A | 11/1980 | Heller et al. |
| 4,310,690 A | 1/1982 | Cummins |
| 4,317,779 A | 3/1982 | Crawford |
| 4,353,942 A | 10/1982 | Carey |
| 4,388,327 A | 6/1983 | Cummins |
| 4,395,363 A | 7/1983 | Crawford |
| 4,419,198 A | 12/1983 | Breda |
| 4,435,527 A | 3/1984 | Cuscurida |
| 4,451,486 A | 5/1984 | Baker |
| 4,524,077 A | 6/1985 | Ruest |

(Continued)

FOREIGN PATENT DOCUMENTS

| CN | 104754956 A | 7/2015 |
| EP | 0079164 A1 | 5/1983 |

(Continued)

OTHER PUBLICATIONS

Koban et al.; J. Agric. Food Chem.; (1984) 32, pp. 393-396.
USDA National Nutrient Database for methionine; 81-pages; downloaded Feb. 11, 2015.
U.S. Appl. No. 13/763,135; Office Action dated Feb. 18, 2015.
U.S. Appl. No. 13/763,101; Office Action dated Jun. 24, 2014.
U.S. Appl. No. 13/763,101; Office Action dated Nov. 22, 2013.
U.S. Appl. No. 13/763,101; Notice of Allowance dated Dec. 8, 2014.

(Continued)

*Primary Examiner* — Susan Tran
(74) *Attorney, Agent, or Firm* — POLSINELLI PC

(57) ABSTRACT

The invention relates to matrix and layer compositions comprising a first polymer. The matrix and layer compositions are useful in the delivery of bioactives. In particular, the matrices and layers may have advantageous properties including mechanical properties and protection of bioactives and may also provide for pH-dependent release of a bioactive.

30 Claims, 14 Drawing Sheets
(14 of 14 Drawing Sheet(s) Filed in Color)

(56) References Cited

U.S. PATENT DOCUMENTS

| | | |
|---|---|---|
| 4,579,962 A | 4/1986 | Takano |
| 4,720,484 A | 1/1988 | Vincent |
| 4,727,163 A | 2/1988 | Bellis |
| 4,777,289 A | 10/1988 | Ruest |
| 4,835,293 A | 5/1989 | Bhatia |
| 4,855,495 A | 8/1989 | Takano |
| 4,883,911 A | 11/1989 | Ruest |
| 5,274,073 A | 12/1993 | Gruber |
| 5,294,605 A | 3/1994 | Houghten |
| 5,310,599 A | 5/1994 | Ford |
| 5,326,887 A | 7/1994 | Di Cosimo |
| 5,357,001 A | 10/1994 | Grosse-Bley |
| 2,703,316 A | 3/1995 | Schneider |
| 5,399,665 A | 3/1995 | Barrera |
| 5,503,852 A | 4/1996 | Steiner |
| 5,602,229 A | 2/1997 | Malabrba |
| 6,008,261 A | 12/1999 | Genova |
| 6,172,067 B1 | 1/2001 | Ito |
| 6,180,643 B1 | 1/2001 | Zablocki |
| 6,518,243 B1 | 2/2003 | Kahne |
| 6,727,285 B1 | 4/2004 | Haik, Jr. |
| 6,939,693 B2 | 9/2005 | Lorbert |
| RE39,403 E | 11/2006 | Robert |
| 7,250,433 B2 | 7/2007 | Barta |
| 7,381,416 B2 | 6/2008 | Erdelmeir |
| 7,714,077 B2 | 5/2010 | Tanaka |
| 7,989,532 B2 | 8/2011 | Li |
| 2001/0008904 A1 | 7/2001 | Robert |
| 2003/0143366 A1 | 7/2003 | Foley |
| 2003/0143661 A1 | 7/2003 | Lorbert |
| 2007/0053866 A1 | 3/2007 | Abou-Nemeh |
| 2007/0231377 A1 | 10/2007 | Abou-Nemeh |
| 2007/0231437 A1 | 10/2007 | Knight |
| 2008/0019860 A1 | 1/2008 | Abou-Nemeh |
| 2008/0241223 A1 | 10/2008 | Nivaggioli |
| 2009/0200511 A1 | 8/2009 | Allen |
| 2010/0048586 A1 | 2/2010 | Deigin |
| 2010/0094043 A1 | 4/2010 | Fujita |
| 2010/0098801 A1 | 4/2010 | Kobler |
| 2011/0021461 A1 | 1/2011 | Vazquez-Anon |
| 2011/0070188 A1 | 3/2011 | Flowers |
| 2011/0295006 A1 | 12/2011 | Kobler |
| 2012/0128616 A1 | 5/2012 | Voisin |
| 2013/0209391 A1* | 8/2013 | Arhancet ............... C08G 67/00 424/78.37 |

FOREIGN PATENT DOCUMENTS

| | | |
|---|---|---|
| EP | 2812313 | 8/2013 |
| EP | 2812372 | 8/2013 |
| EP | 2812313 | 12/2014 |
| EP | 2812372 | 12/2014 |
| EP | 2871973 | 6/2016 |
| JP | 2004001190 A | 1/2004 |
| JP | 2005232046 A | 2/2005 |
| JP | 2005232047 A | 9/2005 |
| JP | 2008239601 A | 10/2008 |
| JP | 2015508076 A | 3/2015 |
| WO | 9215547 A1 | 9/1992 |
| WO | 9509142 A1 | 4/1995 |
| WO | 9636314 A2 | 11/1996 |
| WO | 9832735 A1 | 7/1998 |
| WO | 9851260 A2 | 11/1998 |
| WO | 9904647 A1 | 2/1999 |
| WO | 0142333 A2 | 6/2001 |
| WO | 0149273 A2 | 7/2001 |
| WO | 02088667 A2 | 11/2002 |
| WO | 03010157 A1 | 2/2003 |
| WO | 03082836 A1 | 10/2003 |
| WO | 2005077882 A1 | 8/2005 |
| WO | 2009088879 A1 | 7/2009 |
| WO | 2009127009 A1 | 10/2009 |
| WO | 2010012712 A1 | 2/2010 |
| WO | 2010048586 A1 | 4/2010 |
| WO | 2010100390 A1 | 9/2010 |
| WO | 2011084466 A1 | 7/2011 |
| WO | 2011084620 A2 | 7/2011 |
| WO | 2011028007 A2 | 10/2011 |
| WO | 2013119955 A1 | 8/2013 |
| WO | 2013119959 A1 | 8/2013 |
| WO | 2014011857 A1 | 1/2014 |

OTHER PUBLICATIONS

European Patent Office; PCT/US2013/025351; Extended European Search Report dated Jan. 9, 2015.

European Patent Office; PCT/US2013/025355; Extended European Search Report dated Aug. 24, 2015.

Leemhuis, "A Versatile Route to Functionalized Dilactones as Monomers for the Synthesis of Poly(a-Hydroxy) Acids," Eur. J. Org. Chem., 2003, pp. 3344-3349.

Li et al., "High Throughput Synthesis of Peptide α-Thioesters Through the Use of "Volatilizable" Support", Journal of Combinatorial Chemistry, 2008, pp. 613-616, vol. 10, No. 5 (and Supporting Information).

Roenne et al., "Lipase-Catalyzed Esterification of Lactic Acid with Straight-Chain Alcohols", J. American Oil Chemists' Society, 2005, pp. 881-885, vol. 82, No. 12.

Sato et al., "Oxidation of sulfides to sulfoxides and sulfones with 30% hydrogen peroxide under organic solvent-and halogen-free conditions", Tetrahedron, 2001, pp. 2469-2476, vol. 57.

Third-Party Submission Under 37 CFR 1.290 from related U.S. Appl. No. 131763,135 dated Apr. 10, 2014 (9 pgs.).

Yoshiizumi et al., "Studies on Scavenger Receptor Inhibitors. Part 1: Synthesis and Structure—Activity Relationships of Novel Derivatives of Sulfatides", Bioorganic & Medicinal Chemistry, 2002, pp. 2445-2460, vol. 10.

European Patent Office; PCT/US2013/050051; Extended European Search Report dated Nov. 25, 2015.

U.S. Appl. No. 14/937,416; Notice of Allowance dated Dec. 16, 2015.

U.S. Appl. No. 13/763,101; Non-final Office Action dated Jun. 24, 2014.

Koban, Kinetics of Hydrolysis of Dimeric and Trimeric Methionine Hydroxy Analogue Free Acid under Physiological Conditions of pH and Temperature, J. Agric. Food Chem., pp. 393-396, vol. 32.

USDA National Nutrient Database for methionine; 81 pages; downloaded Feb. 11, 2015.

Weerden E J Van et al: "Utilization of the Polymers of Methionine Hydroxy Analog Free Acid (MHA-FA) in Broiler Chicks," Archiv Fuer Gefluegelkunde, Verlag Eugen Ulmer GMBH, DE, vol. 56, No. 2, Jan. 1, 1992, pp. 63-68.

Yoshio Hayashi et al: "Analysis of Amide Bond Formation with an [alpha]-Hydroxy-[beta]-amino Acid Derivative, 3-Amino-2-hydroxy-4-phenylbutanoic Acid, as an Acyl Component: Byproduction of Homobislactone," The Journal of Organic Chemistry, vol. 66, No. 16, Aug. 1, 2001, pp. 5537-5544.

In't Veld P J A et al: "Synthesis of Biodegradable Polyesteramides with Pendant Functional Groups," Makromolekulare Chemie, Macromolecular Chemistry and Physics, Wiley—VCH Verlag GMBH & Co. KGAA, vol. 193, No. 11, Nov. 1, 1992, pp. 2713-2730.

Gu S Y et al., "Synthesis and evaluation of a biodegradable material with cell recognition motives," Carbohydrate Polymers, Applied Science Publishers, Ltd., Barking, GB, vol. 74, No. 3, Nov. 4, 2008, pp. 572-578.

Hui Yu et al., "Synthesis and characterization of arginine-glycerine-aspartic peptides conjugated poly(lactic acid-co-l-lysine) diblock copolymer," Journal of Materials Science: Materials in Medicine, Kluwer Academic Publishers, BO, vol. 19, No. 3, Aug. 20, 2007, pp. 1275-1281.

Gerhardt W Wet al., "Functional lactide monomers," Biomacromolecules, American Chemical Society, US, vol. 7, No. 6, Jan. 1, 2006, pp. 1735-1742.

Andrew D. Abell et al., "Synthesis of a [1,4]dioxane-2,5-dione based-peptidomimetric scaffold," Arkivoc, vol. 2006, No. 3, Jan. 1, 2006, pp. 72-76.

(56) References Cited

OTHER PUBLICATIONS

Maryanoff B E et al., "Macrocyclic Peptide inhibitors of serine proteases. Convergent total synthesis of cyclotheonamides a and b via late-stage primary amine intermediate. Study of Thrombin Inhibition Under diverse conditions," Journal of the American Chemical Society, US, vol. 117, No. 4, Jan. 1, 1995, pp. 1225-1239.
Office action dated Jan. 27, 2016 from related Australian Application No. 2013290122, 9 pgs.
English translation of Office action dated May 25, 2016 from related Chinese Application No. 201380047090.3, 9 pgs.
European Search Report dated Nov. 25, 2015 from related European Application No. 13816624.4, 8 pgs.
Bentley et al. "Action of Nitrogen on certain Proteins II. Synthesis of Methionine Sulphoximine and other Sulphoxmines," 1950, 265-272.
Brenner et al. "Isolation of enzymatically manufactured L-methionyl-L-methionine and L-methionyl-L-methionyl-L-methionine; a comparison with synthetic products" Helv. Chim. Acta 1951; 34:2085-2096 (German language document, no translation available).
Bruyer, "Oligomers in Equilibrium in DL-2-Hydroxy-4-Methylthio Butanoic Acid (HMB) Solutions." 1987, dated Jan. 26, 14 pgs.
Bueno et al. "1,4-Dioxane-2,5-dione-type monomers derived from L-ascorbic and D-isoascorbic acids Synthesis and Polymerisation," Carbohydrate Research (2009), 344(15), 2100-2104.
Chen et al. "ProSAR: A new Methodology for Combinatorial Library Design" J. Chem. Inf. Model 2009, 49, 603-614.
Cohen-Arazi, et al. "Preparation of New [alpha]-hydroxy Acids Derived from Amino Acids and Their Corresponding Polyesters," Oct. 28, 2008 Macromolecules, vol. 41, No. 20, 7259-7263, supplemental data.
Dechy-Cabaret, "Controlled Ring-Opening Polymerization of Lactide and Glycolide" Chem. Rev. 2004 104 (12), 6147-6176.
Franz et al. "Synthesis of Functional Polydepsipeptides via Direct Ring-Opening Polymerization and Post-Polymerization Modification" Macromolecular Journals; Macromol. Chem. Phys. 2010, 211, 809-820.
Gerhardt et al. "Functional Lactide Monomers: Methodology and Polymerization" Biomacromolecules Jun. 2006, 7 (6):1735-1742.
Gu, "Carbohydrate Polymers," Carbohydrate Polymers 74 (2008) 572-578.
Hutamacher, "Polyhydroxymethionine" Biopolymers, vol. 9, pp. 81-87, 2003 Wiley-VCH.
Jiang et al. "Clickable" Polyglycolides: Tunable Synthons for Thermoresponsive, Degradable Polymers; Macromolecules 2008, 41, 1937-1944.
Jing et al. "Cyclohexyl-substituted polyglycolides with high glass transition temperatures" Macromolecules (2007), 40 (26), 9304-9312.
Jost et al. "Papain catalyzed oligomerization of α-amino acids. Synthesis and characterization of water-insoluble oligomers of L-methionine" Helv. Chim. Acta, 1980;63:375-384.
Kasai et al. "Correlation between molecular weight distribution of oligo-L-methionine prepared by papain-catalyzed polymerization and its supplementary effect in a low protein diet." 1992 Biosci., Biotechnol., Biochem. 56: 1884-1885.
Kolitz et al. "Biodegradable Polyesters Derived from Amino Acid," Macromolecules Article 2009, 42, 4520-4530.
Lee et al. "Papain catalyzed polymerization of L-α-amino acid methyl esters with hydrophobic side chains," Chem. Express 1990;5:741-744.
Leemhuis et al. "Synthesis and characterization of allyl functionalized poly(α-hydroxy)acids and their further dihydroxylation and epoxidation," European Polymer Journal (2008), 44(2), 308-317.
Noga et al. "Synthesis and Modification of functional Poly(lactide) Copolymers: Toward Biofunctional Materials" Biomacromolecules 2008, 9, 2056-2062.
Nguyen et al. "Polydepsipeptides: Investigation of Secondary Structure" PMSE Preprints Fall 2009, vol. 101,16-20, vol. 2 of 2, 798-799, American Chemical Society Division of Polymeric Materials: Science and Engineering Fall 2009.
Ouchi et al. "Design of Lactide-Based Copolymers for Biomaterials," Polymer Preprints Fall 2002, 43 (2) 648-649.
Ouchi et al. "Preparation of Poly(L-lactide)—Based Microspheres Having a Cationic or Anionic Surface Using Biodegradable Surfactants" Published by the American Chemical Society, Sep./Oct. 2002; vol. 3 No. 5, 885-888.
Ouchi et al. "Synthesis of a block copolymer of L-lactide and depsipetide with pendant thiol groups," Designed Monomers and Polymers, vol. 3, No. 3. pp. 279-287 (2000).
Pounder et al. "Synthesis and Organocatalytic Ring-Opening Polymerization of Cyclic Esters Derived from L-Malic Acid," Biomacromolecules (2010), 11, 1930-1939.
Qi et al. "Cytotoxicity and Cellular Uptake Evaluation of Mitoxantrone-Loaded Poly(lactic acid-co-lysine) Arginine-Glycine-Aspartic Acid Nanoparticles," Journal of Applied Polymer Science 2010, vol. 119, 1011-1015.
Rajesh et al. "Enzymatic Synthesis and Characterization of L-Methionine and 2-Hydroxy-4-(methylthio)butanioc Acid (HMB) Co-oligomers," 2003 J. Agric. Food Chem. 51, 2461-2467.
Reynal, "Omasal Flow of Soluble Proteins, Peptides, and Free Amino Acids in Dairy Cows Fed Diets Supplemented with Proteins of Varying Ruminal Degradabilities" (2007) J. Dairy Sci. 90:1887-1903.
Ristic et al. "The Properties of Poly(L-Lactide) Prepared by Different Synthesis Procedure," Journal of Polymers and the Environment (2011), 19(2), 419-430.
Rubenshtein et al "Facile Procedure for Generating Side Chain Functionalized Poly(r-hydroxyacid) Copolymers from Aldehydes via a Versatile Passerini-Type Condensation," Org. Lett, 2010, vol. 12, No. 15, pp. 3560-3563.
Williams et al. "Synthesis of functionalized biodegradable polyesters" Tutorial Review 2007, vol. 36, 1573-1580.
Yan et al. "Synthesis and RGD peptide of Poly {(lactic acid)-co-[(glycolic axid)-alt-L-lysine)]}" 2008, e-Polymers, No. 028, 12 pgs.
Yin et al. "Preparation and Characterization of Substituted Polylactides" Macromolecules (Nov. 16, 1999), 32(23), 7711-7718.
Yin et al. "Synthesis and characterization of substituted polylactides," Polymer Preprints (1998), 39(2), 158-159, American Chemical Society.
Yu et al. "Synthesis of 3-benzyl-glyceric acid: a key intermediate of a novel cyclic ester monomer" Chinese Journal of Polymer Science (2002), 20(2), 177-180.
International Search Report and Written Opinion for PCT/US2013/025355 dated Apr. 22, 2013.
International Search Report and Written Opinion for PCT/US2013/025351 dated Apr. 22, 2013.
International Search Report and Written Opinion for PCT/US2013/50051 dated Dec. 6, 2013.
Non Final Rejection for U.S. Appl. No. 13/763,101 dated Nov. 22, 2013.
Hayashi, Y., "Analysis of Amide Bond Formation with an a-Hydroxy-B-amino acid derivative, 3-amino-2-hydroxy-4-phenylbutanoic Acid, as an Acyl Component Byproduction of Homobislactone," J. Org. Chem. (2001), 5537-5544.
Notice of Allowance dated Dec. 8, 2014 from related U.S. Appl. No. 13/763,101.
Balg et al., "Inhibition of Helicobacter pylori Aminoacyl-tRNA Amidotransferase by Puromycin Analogues", J. Am. Chem. Soc., 2008, pp. 3264-3265, vol. 130, No. 11.
Clint et al., "Thermodynamics of Micellization of Homologous Series of n-Alkyl Methyl Sulphoxides and n-Alkyl (dimethyl)phosphine Oxides", J. Chem. Soc., Faraday Transactions 1, 1975, pp. 946-954, vol. 71.
Clint, "Micellization of Mixed Nonionic Surface Active Agents", J. Chem. Soc., Faraday Transactions 1, 1975, pp. 1327-1334, vol. 71.
Evans et al., "Nanomolar-Affinity, Non-Peptide Oxytocin Receptor Antagonists", Journal of Medicinal Chemistry, 1993, pp. 3993-4005, vol. 36, No. 25.
Hennaux et al., "Novel nonionic polymerisable surfactants based on sulfoxides. 1. Monomer synthesis and general surfactant behaviour", Colloid Polym. Sci., 2001, pp. 1149-1159, vol. 279.

(56) References Cited

OTHER PUBLICATIONS

Hennaux et al., "Novel nonionic surfactants based on sulfoxides. 2. Homo- and copolymers", Colloid Polym. Sci., 2003, pp. 807-814, vol. 281.

Ignasiak et al., "Characterization by mass spectrometry and IRMPD spectroscopy of the sulfoxide group in oxidized methionine and related compounds", Chemical Physics Letters, 2011, pp. 29-36, vol. 502.

International Search Report and Written Opinion for PCT/US2012/072016 dated Mar. 5, 2013.

John, "Synthese and Modification of New Biodegradable Copolymers: Serine/Glycolic Acid Based Copolymers, New Biodegradable Copolymers," 1997, pp. 1901-1907.

Komori et al., "Structure Activity Relationships of Synthetic Antibiotic Analogues of Chryscandin", The Journal of Antibiotics, 1985, pp. 1182-1203, vol. 38, No. 9.

\* cited by examiner

Hours 0-16 at pH 6.5, Hours 16-18 at pH 2.5, Hours 18-40 at pH 6.5

MATRIX AND LAYER COMPOSITIONS FOR PROTECTION OF BIOACTIVES

CROSS-REFERENCE TO RELATED APPLICATIONS

This application is a continuation application of U.S. patent application Ser. No. 14/413,540, now U.S. Pat. No. 9,452,143, filed Jan. 8, 2015, which is a U.S. National Stage Application of PCT International Application No. PCT/US2013/050051, filed Jul. 11, 2013, which claims the benefit of priority of U.S. Provisional Application Ser. No. 61/670,817, filed Jul. 12, 2012, the disclosure of each is hereby incorporated by reference in its entirety.

FIELD OF THE INVENTION

The invention relates to matrix and layer compositions. The matrix and layer compositions are useful in the delivery and protection of bioactives.

BACKGROUND OF THE INVENTION

Supplementing human and animal diets with essential amino acids and/or other bioactive agents improves health and performance. Bioactives may be sensitive to degradation, yet need to be provided with a particular release profile. Combining the bioactive in a particular matrix composition or with a layer coating composition comprising a polymer is one way to deliver protected bioactives with a desired release profile. Providing amino acids and/or bioactive agents to ruminants, in particular, is challenging because microbes in the rumen may digest and degrade the bioactive agent of interest before it can be absorbed and utilized by the animal. Over the years, various protection approaches have been taken, but with mixed results. What is needed, therefore, is an improved means for protecting bioactive agents. In particular, compositions that provide pH-dependent release provide advantages in the delivery of bioactives.

SUMMARY OF THE INVENTION

In one aspect of the present disclosure, a composition comprising a layer formed over a core is provided. The core comprises a bioactive agent and the layer comprises a first polymer comprising a repeat unit of Formula (I):

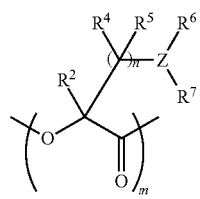

(I)

wherein,
$R^2$, $R^4$, and $R^5$ are independently hydrogen, hydrocarbyl, or substituted hydrocarbyl;
$R^6$ is hydrogen, hydrocarbyl, or substituted hydrocarbyl;
$R^7$ is optionally present, when present it is hydrogen, hydrocarbyl, or substituted hydrocarbyl;
Z is sulfur, sulfone, sulfoxide, or selenium;
n is an integer $\geq 1$; and
m is an integer $>1$.

In another aspect of the present disclosure, an agglomerated composition comprising a plurality of bioactives embedded in a matrix is provided. The matrix comprises a first polymer comprising a repeat unit of Formula (I):

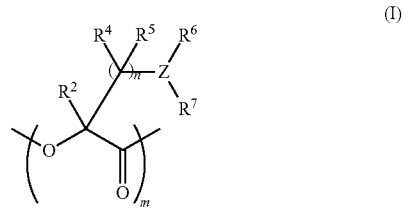

(I)

wherein,
$R^2$, $R^4$, and $R^5$ are independently hydrogen, hydrocarbyl, or substituted hydrocarbyl;
$R^6$ is hydrogen, hydrocarbyl, or substituted hydrocarbyl;
$R^7$ is optionally present, when present it is hydrogen, hydrocarbyl, or substituted hydrocarbyl;
Z is sulfur, sulfone, sulfoxide, or selenium;
n is an integer $\geq 1$; and
m is an integer $>1$.

Other iterations of the disclosure are provided in more detail below.

BRIEF DESCRIPTION OF THE DRAWINGS

The patent or application file contains at least one drawing executed in color. Copies of this patent or patent application with color drawing(s) will be provided by the Office by request and payment of the necessary fee.

FIG. 1A shows release from prototype 1. FIG. 1B presents release from prototype 2. FIG. 1C shows release from prototypes 3 and 4. FIG. 1D presents release from prototype 5. FIG. 1E shows release from prototypes 6 and 7.

FIG. 2A presents the percentage of dry matter remaining as a function of time in the rumen. FIG. 2B presents the percentage of dry matter remaining at 24 hours for each sample.

DETAILED DESCRIPTION OF THE INVENTION

Figure 1A:
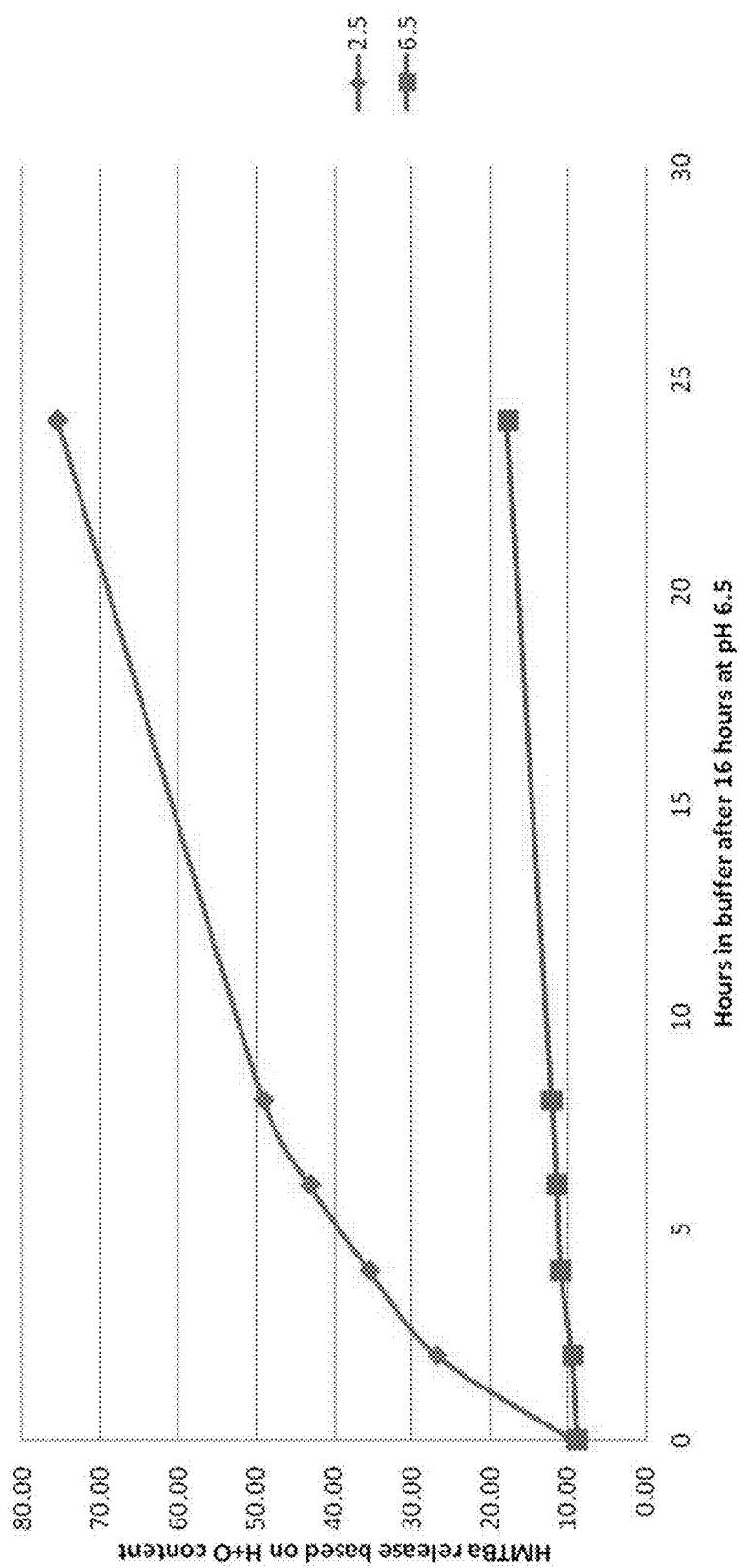
FIGS. 1A-E document pH-dependent release of 2-hydroxy-4-methylthiobutanoic acid (HMTBa) from various preparations of coated particles, which are described in Tables 1 and 2. Shown is the release at pH 2.5 or 6.5 as a function of time.
Figure 1B:
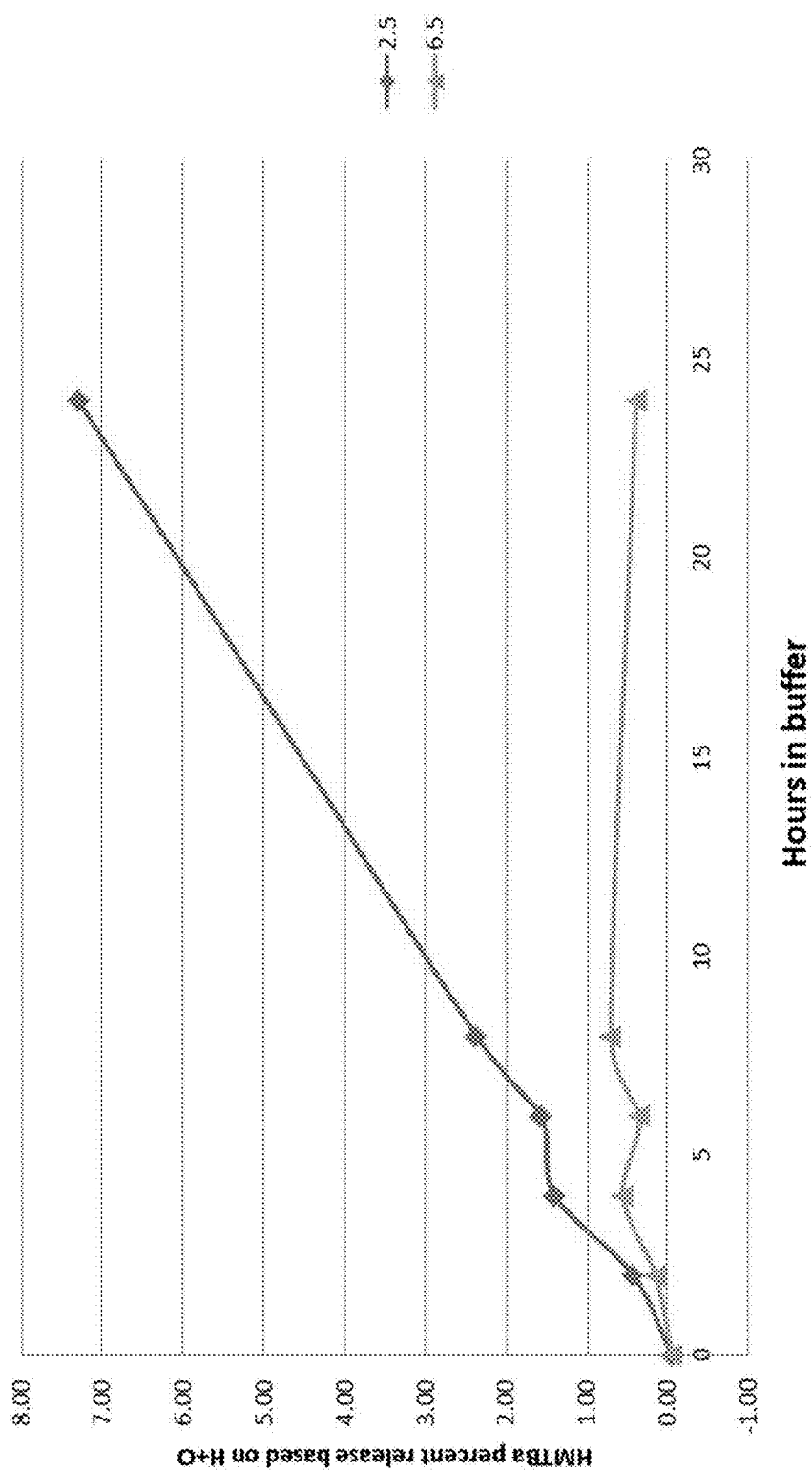

I. Composition Comprising a Layer Formed Over a Core

The present disclosure provides a composition comprising a layer formed over a core. As described in further detail herein, the layer comprises a first polymer having a repeat unit of Formula (I) and the core comprises a bioactive.

(a). Layer

The layer of the composition comprises a first polymer. The first polymer comprises a repeat unit of Formula (I):

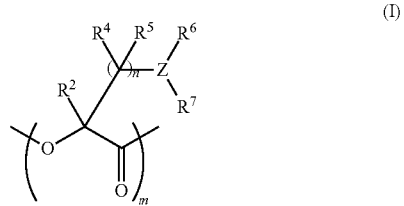

wherein,
$R^2$, $R^4$, and $R^5$ are independently chosen from hydrogen, hydrocarbyl, and substituted hydrocarbyl;
$R^6$ is chosen from hydrogen, hydrocarbyl, and substituted hydrocarbyl;
$R^7$ is optionally present, when present it is chosen from hydrogen, hydrocarbyl, and substituted hydrocarbyl;
Z is chosen from sulfur, sulfone, sulfoxide, and selenium;
n is an integer $\geq 1$; and
m is an integer $>1$.

In some embodiments, $R^2$ may be chosen from hydrocarbyl, substituted hydrocarbyl, and hydrogen. In some embodiments, $R^2$ may be a lower chain alkyl groups including methyl, ethyl, propyl, butyl, pentyl, and hexyl. In another embodiment, $R^2$ may be phenyl, benzyl, or substituted phenyl or benzyl. In preferred embodiments, $R^2$ may be hydrogen.

$R^4$ and $R^5$ are independently chosen from hydrogen, hydrocarbyl, and substituted hydrocarbyl. The —$(CR^4 R^5)_n$— may constitute a hydrocarbyl chain which may be linear or branched, with n representing the number of linked carbon atoms in the chain. In various embodiments, n may be equal to or greater than 1. In some embodiments, n may range from 1 to 20 and the hydrocarbyl chain comprises from 1 to 20 linked carbon atoms. In one embodiment, n may range from 1 to 5. In still another embodiment, n may be equal to 2, 3, 4, 5, 6, 7, 8, 9, 10, 11, 12, 13, 14, 15, 16, 17, 18, 19, or 20. $R^4$ and $R^5$ may be hydrogen throughout the chain, in other aspects select $R^4$ and $R^5$ may be hydrocarbyl or substituted hydrocarbyl.

Formula (I) also contains a heteroatom Z group. In some embodiments, the Z may be selenium, sulfur, sulfoxide, or sulfone groups. The selenium, or sulfur atoms may be charged and/or be present in various oxidation states within the molecule. Where the Z carries a charge, the composition may further comprise a counterion including, but not limited to lithium, sodium, potassium, calcium, magnesium, and the like.

$R^6$ in Formula (I) may be chosen from hydrogen, hydrocarbyl, and substituted hydrocarbyl. Where $R^6$ is a hydrocarbyl, it may be any alkyl chain but is preferably a lower chain alkyl group such as methyl, ethyl, propyl, butyl, pentyl, or hexyl. The lower alkyl groups may additionally be branched or cyclic. Non-limiting examples include isopropyl, isobutyl, sec-butyl, t-butyl, cyclopropyl, cyclobutyl, cyclopentyl, and the like. In another embodiment, $R^6$ may be phenyl, benzyl, or substituted phenyl or benzyl. In an exemplary embodiment, $R^6$ may be methyl.

$R^7$ may be optionally present in the repeat unit comprising Formula (I). When present $R^7$, is chosen from hydrocarbyl, substituted hydrocarbyl, and hydrogen. Where $R^7$ is a hydrocarbyl, it may be any alkyl group but is preferably a lower chain alkyl group such as methyl, ethyl, propyl, butyl, pentyl, or hexyl. The lower alkyl groups may additionally be branched or cyclic, non-limiting examples include isopropyl, isobutyl, sec-butyl, t-butyl, cyclopropyl, cyclobutyl, cyclopentyl, and the like. In another embodiment, $R^7$ may be phenyl, benzyl, or substituted phenyl or benzyl. In a further embodiment, $R^7$ may be hydrogen.

The molecular weight of the first polymer can and will vary in different embodiments. The variable m represents the number of repeat units in the polymer. Generally, m is greater than 1. In one embodiment, m is greater than 2, 3, 4, 5, 6, 7, 8, 9, 10, 11, 12, 13, 14, 15, 16, 17, 18, 19, or 20. In other embodiments, m may be greater than 20. In particular embodiments, m ranges from 2 to 10.

In some embodiments, the molecular weight of the first polymer may be at least 500 Da, or at least 600 Da, or at least 700 Da, or at least 800 Da, or at least 900 Da, or at least 1,000 Da, or at least 1,100 Da, or at least 1,200 Da, or at least 1,300 Da, or at least 1,400 Da, or at least 1,500 Da, or at least 1,600 Da, or at least 1,700 Da, or at least 1,800 Da, or at least 1,900 Da, or at least 2,000 Da. In another aspect, the molecular weight of the polymer may range from 800 Da to about 10,000 Da, or from about 2,000 Da to about 5,000 Da, or from about 2,000 Da to about 10,000 Da. In a further embodiment, the molecular weight of the polymer may be greater than about 10,000 Da. The weight of a mixture of polymers may be characterized by its weight-average molecular weight. In some aspects, the weight-average molecular weight of the polymers may be at least 500 Da, or at least 600 Da, or at least 700 Da, or at least 800 Da, or at least 900 Da, or at least 1,000 Da, or at least 1,100 Da, or at least 1,200 Da, or at least 1,300 Da, or at least 1,400 Da, or at least 1,500 Da, or at least 1,600 Da, or at least 1,700 Da, or at least 1,800 Da, or at least 1,900 Da, or at least 2,000 Da. In other aspects, the weight-average molecular weight may be about 2,000 Da, about 3,000 Da, about 4,000 Da, or about 5,000 Da. The molecular weight may be determined by gel permeation chromatography or other means known in the art.

In certain embodiments, the first polymer may also be characterized by a monomer percent. A monomer percent is the percent of the polymer composition which is monomeric. In some aspects, the monomer percent is less than 20%. In other aspects, the monomer percent is less than 15%. More preferably, the monomer percent is less than 10%. In various aspects, the monomer percent is less than 9%, less than 8%, less than 7%, less than 6%, less than 5%, less than 4%, less than 3%, less than 2%, or less than 1%.

In one preferred embodiment, the first polymer comprises a repeat unit comprising Formula (II):

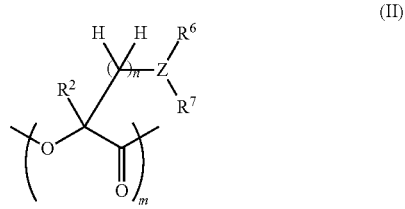

wherein, $R^2$, $R^6$, $R^7$, Z, n, and m are as defined for Formula (I).

In another alternative embodiment, the first polymer comprises a repeat unit comprising Formula (IIa):

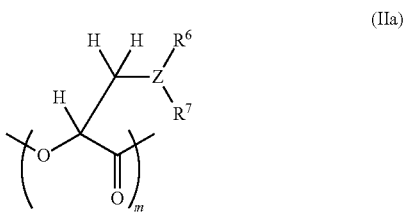

wherein, $R^6$, $R^7$, and m are as defined for Formula (I) and Z is selected from sulfur, sulfone, sulfoxide, and selenium.

In another exemplary embodiment, the first polymer comprises a repeat unit comprising Formula (III):

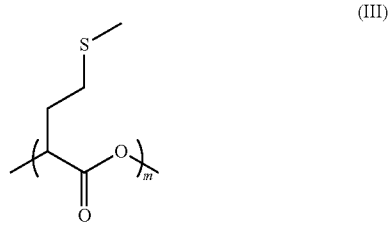

wherein, m is as defined for Formula (I).

In some aspects of the invention, the first polymer may have chiral centers. In particular, the carbon alpha to the carbonyl unit in the compound of Formula (I), (II), or (III) may be chiral and may have an R or an S configuration. In some embodiments, the configuration at this position may be R. In other embodiments, the configuration at this position may be S. In various aspects, the repeat units may be all R, all S, or comprise a combination of R and S repeat units, for example, the configuration of the repeat units may alternate in block or randomly.

The layer comprising the first polymer may comprise at least one additional agent. The additional agent may be chosen from polymers, including crystalline and semi-crystalline polymers. Examples of suitable polymers, without limitation, are polymers of acrylates, aminoacrylates, alkylene succinates, alkylene oxalates, amides, amino acids, anhydrides, arylates, carbonates, cellulose (including, but not limited to, hydroxymethylcellulose, hydroxypropylcellulose, methylcellulose, carboxymethyl cellulose and ethylcellulose), caprolactone, cyanoacrylates, dihydropyrans, dioxanes, dioxanones, ether ether ketones, ethylene glycol, fumarates, hydroxyalkanoates, hydroxyl-esters, imides, ketals, lactides, methacrylates, methyl olefins, orthoesters, phosphazines, styrenes, terephthalates, trimethylene carbonate, urathanes, vinyl acetates, vinyl ketones, vinyl halides, derivatives, isomers, and mixtures thereof. The additional agent may also be a wax, including natural and synthetic waxes; fatty acids, including $C_{12}$-$C_{30}$ fatty acids, and fatty acid esters, including monogylcerides, diglycerides, and triglycerides. Non-limiting examples include canola oil, coconut oil, corn oil, cottonseed oil, lauric acid, linoleic acid, oleic acid, palm oil, palmitic acid, soy oil, soybean oil, stearic acid, stearin, sunflower seed oil, vegetable oil, and combinations thereof. The oils may be hydrogenated, non-hydrogenated, or partially hydrogenated. The additional agent may be a flow agent, including carbonates and talcs and combinations thereof. Carbonates may be selected from copper carbonate, zinc carbonate, calcium carbonate, magnesium carbonate, potassium carbonate, sodium carbonate, and combinations thereof.

In one embodiment, the additional agent is a pH-sensitive polymer and may be chosen from natural and modified polymers (e.g. chitosan) including blends with monomers. The additional agents may be amino type polymers. Amino type polymers include, but are not limited to, pyridine, pyridine derivatives, amino acrylate type monomers, such as dialkylamino ethyl acrylate, styrene, styrene derivatives (such as poly-2-vinylpyridine-co-styrene), acrylonitrile, acrylate type monomers of acrylic acid, vinyl esters, vinyl acetate, and vinyl substituted heterocyclic rings that contain nitrogen fusions (such as vinyl carbazole, vinyl quinolone and N-vinylpyrrole). In one preferred embodiment, the additional agent is poly-2-vinylpyridine-co-styrene.

In one alternative embodiment, the layer composition is free of ethylcellulose.

In some embodiments, the first polymer comprises 100% of the layer. In other embodiments, the first polymer is about 5% to about 50% by weight of the layer and the additional agent comprises from about 50% to about 95% by weight of the layer. In various embodiments, the additional agent comprises about 50%, 60%, 70%, 80%, or 90% of the layer. In embodiments where two or more additional agents are provided in the layer, each agent may be provided in any ratio without limitation.

The total weight percentage of the layer can and will vary. In some embodiments, the layer ranges from about 1% to about 50% by weight of the total composition. More preferably, the layer ranges from about 5% to about 15% by weight, or from about 8% to about 12% by weight. In some embodiments, the total weight percentage of the layer less than about 1%), less than about 2%, less than about 3%, less than about 4%, less than about 5%, less than about 6%, less than about 7%, less than about 8%, less than about 9%, less than about 10%, less than about 11%, less than about 12%, less than about 13%, less than about 14% or less than about 15% by weight.

(b). Core

The composition further comprises a core comprising a bioactive. In some embodiments, the core contains one bioactive. In other embodiments, the core contains more than one bioactive. When more than one bioactive is present in the core, they can be provided in any ratio. For example, when two bioactives are present they can be present in a ratio of about 99:1, 95:5, 90:10, 85:15, 80:20, 75:25, 70:30, 65:35, 60:40, 55:45, or 50:50 by weight percent, or at any ratio between the listed ratios. When more than two bioactives are present, they may similarly be present in any ratio without limitation.

The bioactive can be present in the core composition in a weight of about 20% to about 90% of the total composition. In some embodiments the bioactive is about 10%, about 15%, about 20%, about 25%, about 30%, about 35%, about 40%, about 45%, about 50%, about 55%, about 60%, about 65%, about 70%, about 80%, about 90%, or about 99% by weight of the total composition. In a preferred embodiment, the bioactive is present in an amount of about 80% to about 90%, or 85% to about 95%, or about 95% to about 99% by weight of the total composition.

i. Bioactive

The bioactive may be chosen from any biologically relevant molecule. Non-limiting examples of bioactives include vitamins, minerals (e.g., organic or inorganic), antioxidants, organic acids, poly unsaturated fatty acid ("PUFA")s, essential oils, pharmaceutically active agents, amino acids or amino acid analogues, enzymes, prebiotics, probiotics, herbs, and pigments.

Suitable vitamins include vitamin C, vitamin A, vitamin E, vitamin B12, vitamin K, riboflavin, niacin, vitamin D, vitamin B6, folic acid, pyridoxine, thiamine, pantothenic acid, and biotin. The form of the vitamin may include salts of the vitamin, derivatives of the vitamin, compounds having the same or similar activity of a vitamin, and metabolites of a vitamin.

Suitable organic trace mineral may comprise a metal chelate comprising metal ions and an amino acid ligand. Alternatively, the organic trace mineral may be a metal salt comprising metal ions and an amino acid anion. The metal ions may be selected from the group consisting of zinc ions, copper ions, manganese ions, iron ions, chromium ions, cobalt ions, magnesium ions, calcium ions, and combinations thereof. The amino acids may be selected from the group comprising alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, or their hydroxy analogs. In certain embodiments, the copper and zinc ions are preferably divalent, i.e., each ion carries a charge of $2^+$. The molar ratio of amino acids to metal ions in the chelate molecule may generally vary from 1:1 to 3:1 or higher. Typically, a metal chelate may comprise a mixture of 1:1, 2:1, and 3:1 species. Preferably, the molar ratio of amino acids to metal ion in the chelate molecule may generally vary from 1.5:1 to 2.5:1. In an aqueous medium, the relative proportions of these species are determined by the applicable stability constants. Where the number of ligands equates to the charge on the metal ion, the charge is typically balanced because the carboxyl moieties of the amino acids are in deprotonated form. For example, in the chelate species wherein the metal cation carries a charge of 2+ and the amino acid to metal ratio is 2:1, each of the hydroxy or amino groups is understood to be bound by a coordinate covalent bond to the metal ion. Where the number of ligands exceeds the charge on the metal ion, e.g., in a 3:1 chelate of a divalent metal ion, the amino acids in excess of the charge typically may remain in a protonated state to balance the charge. On the other hand, where the positive charge on the metal ion exceeds the number of amino acids, the charge may be balanced by the presence of another anion such as, for example, chloride, bromide, iodide, bicarbonate, hydrogen sulfate, dihydrogen phosphate and combinations thereof. Divalent anions may also be present. In an exemplary embodiment, the metal chelate comprises 2-hydroxy-4-methylthiobutanoic acid (HMTBa).

The mineral may be an inorganic trace mineral. Suitable inorganic trace minerals include, for example, metal sulfates, metal oxides, metal hydroxides, metal oxychlorides, metal carbonates, and metal halides. By way of non-limiting example, the inorganic trace mineral may be copper sulfate, copper oxide, copper chloride, or copper carbonate. Alternatively, the inorganic trace mineral may be manganese sulfate, manganese chloride, or manganous oxide. In another embodiment, the inorganic trace mineral may be zinc sulfate, zinc oxide, zinc chloride, or zinc carbonate. In yet an additional embodiment, the inorganic trace mineral may be sodium selenite or sodium selenate.

Suitable antioxidants include, but are not limited to, ascorbic acid and its salts, ascorbyl palmitate, ascorbyl stearate, anoxomer, n-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline (ethoxyquin), ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate, flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, n-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, wheat germ oil, zeaxanthin, or combinations thereof.

A variety of organic acids comprised of carboxylic acids are suitable. In one embodiment, the organic acid may contain from about one to about twenty-five carbon atoms. In another embodiment, the organic acid may have from about three to about twenty-two carbon atoms. In a further embodiment, the organic acid may contain from about three to about twelve carbon atoms. In yet another embodiment, the organic acid may contain from about eight to about twelve carbon atoms. In still another embodiment, the organic acid may contain from about two to about six carbon atoms. Suitable organic acids, by way of non-limiting example, include formic acid, acetic acid, propionic acid, butanoic acid, benzoic acid, lactic acid, malic acid, tartaric acid, mandelic acid, citric acid, fumaric acid, sorbic acid, boric acid, succinic acid, adipic acid, glycolic acid, cinnamaldehyde, and glutaric acid.

Salts of organic acids comprising carboxylic acids are also suitable for certain embodiments. Representative suitable salts include the ammonium, magnesium, calcium, lithium, sodium, potassium, selenium, iron, copper, and zinc salts of organic acids. In one embodiment, the organic acid is an ammonium, magnesium, calcium, lithium, sodium, potassium, selenium, iron, copper, or zinc salt of formic acid. In another embodiment, the organic acid is an ammonium, magnesium, calcium, lithium, sodium, potassium, selenium, iron, copper, or zinc salt of acetic acid. In yet another embodiment, the organic acid is an ammonium, magnesium, calcium, lithium, sodium, potassium, selenium, iron, copper, or zinc salt of propionic acid. In an additional embodiment, the organic acid is an ammonium, magnesium, calcium, lithium, sodium, potassium, selenium, iron, copper, or zinc salt of butanoic acid. In a further embodiment, the organic acid is an ammonium, magnesium, calcium, lithium, sodium, potassium, selenium, iron, copper, or zinc salt of benzoic acid. In still another embodiment, the organic acid is an ammonium, magnesium, calcium, lithium, sodium, potassium, selenium, iron, copper, or zinc salt of lactic acid. In yet another embodiment, the organic acid is an ammonium, magnesium, calcium, lithium, sodium, potassium, selenium, iron, copper, or zinc salt of malic acid. In still another embodiment, the organic acid is an ammonium, magnesium, calcium, lithium, sodium, potassium, selenium, iron, copper, or zinc salt of tartaric acid. In a further embodiment, the organic acid is an ammonium, magnesium, calcium, lithium, sodium, potassium, selenium, iron, copper, or zinc salt of mandelic acid. In yet another embodiment, the organic acid is an ammonium, magnesium, calcium, lithium, sodium, potassium, selenium, iron, copper, or zinc salt of citric acid. In an additional embodiment, the organic acid is an ammonium, magnesium, calcium, lithium, sodium, potassium, selenium, iron, copper, or zinc salt of fumaric acid. In an additional embodiment, the organic acid is an ammonium, magnesium, calcium, lithium, sodium, potassium, selenium, iron, copper, or zinc salt of sorbic acid. In another embodiment, the organic acid is an ammonium, magnesium, calcium, lithium, sodium, potassium, selenium, iron, copper, or zinc salt of boric acid. In yet another embodiment, the organic acid is an ammonium, magnesium, calcium, lithium, sodium, potassium, selenium, iron, copper, or zinc salt of succinic acid. In another embodiment, the organic acid is an ammonium, magnesium, calcium, lithium, sodium, potassium, selenium, iron, copper, or zinc salt of adipic acid. In yet another embodiment, the organic acid is an ammonium, magnesium, calcium, lithium, sodium, potassium, selenium, iron, copper, or zinc salt of glycolic acid. In an additional embodiment, the organic acid is an ammonium, magnesium, calcium, lithium, sodium, potassium, selenium, iron, copper, or zinc salt of glutaric acid.

Alternatively, the organic acid may be comprised of a substituted carboxylic acid. A substituted carboxylic acid generally has the same features as those detailed above for carboxylic acids, but the hydrocarbyl chain has been modified such that it is branched, is part of a ring structure, or contains some other substitution. In one embodiment, the substituted carboxylic acid may contain one or more additional carboxyl groups. Saturated dicarboxylic acids include malonic acid, succinic acid, glutaric acid, and adipic acid, and unsaturated dicarboxylic acids include maleic acid and fumaric acid. In another embodiment, the substituted carboxylic acid may contain one or more hydroxy groups. A substituted carboxylic acid with a hydroxy group on the alpha carbon, i.e., the carbon adjacent to the carboxyl carbon, is generally called a α-hydroxy carboxylic acid. Examples of suitable α-hydroxy carboxylic acids include glycolic acid, lactic acid, malic acid, and tartaric acid. In an alternate embodiment, the substituted carboxylic acid may contain one or more carbonyl groups. In yet another embodiment, the substituted carboxylic acid may contain an amino group on the alpha carbon, i.e., is an α-amino acid. In one embodiment, the α-amino acid may be one of the twenty standard amino acids or derivatives thereof. In another embodiment, the α-amino acid may be an essential α-amino acid selected from the group consisting of arginine, histidine, isoleucine, leucine, lysine, methionine, phenylalanine, threonine, tryptophan, and valine. Salts of organic acids comprising substituted carboxylic acids are also suitable for certain embodiments. Representative suitable salts include the ammonium, magnesium, calcium, lithium, sodium, potassium, selenium, iron, copper, and zinc salts of organic acids comprising substituted carboxylic acids.

Suitable PUFAs include a long chain fatty acid with at least 18 carbon atoms and at least two carbon-carbon double bonds, generally in the cis-configuration. In an exemplary embodiment, the PUFA is an omega fatty acid. The PUFA may be an omega-3 fatty acid in which the first double bond occurs in the third carbon-carbon bond from the methyl end of the carbon chain (i.e., opposite the carboxyl acid group). Suitable examples of omega-3 fatty acids include all-cis 7,10,13-hexadecatrienoic acid; all-cis-9,12,15-octadecatrienoic acid (alpha-linolenic acid, ALA); all-cis-6,9,12,15,-octadecatetraenoic acid (stearidonic acid); all-cis-8,11,14,17-eicosatetraenoic acid (eicosatetraenoic acid); all-cis-5,8,11,14,17-eicosapentaenoic acid (eicosapentaenoic acid, EPA); all-cis-7,10,13,16,19-docosapentaenoic acid (clupanodonic acid, DPA); all-cis-4,7,10,13,16,19-docosahexaenoic acid (docosahexaenoic acid, DHA); all-cis-4,7,10,13,16,19-docosahexaenoic acid; and all-cis-6,9,12,15,18,21-tetracosenoic acid (nisinic acid). In an alternative embodiment, the PUFA may be an omega-6 fatty acid in which the first double bond occurs in the sixth carbon-carbon bond from the methyl end of the carbon chain. Examples of omega-6 fatty acids include all-cis-9,12-octadecadienoic acid (linoleic acid); all-cis-6,9,12-octadecatrienoic acid (gamma-linolenic acid, GLA); all-cis-11,14-eicosadienoic acid (eicosadienoic acid); all-cis-8,11,14-eicosatrienoic acid (dihomo-gamma-linolenic acid, DGLA); all-cis-5,8,11,14-eicosatetraenoic acid (arachidonic acid, AA); all-cis-13,16-docosadienoic acid (docosadienoic acid); all-cis-7,10,13,16-docosatetraenoic acid (adrenic acid); and all-cis-4,7,10,13,16-docosapentaenoic acid (docosapentaenoic acid). In yet another alternative embodiment, the PUFA may be an omega-9 fatty acid in which the first double bond occurs in the ninth carbon-carbon bond from the methyl end of the carbon chain, or a conjugated fatty acid, in which at least one pair of double bonds are separated by only one single bond. Suitable examples of omega-9 fatty acids include cis-9-octadecenoic acid (oleic acid); cis-11-eicosenoic acid (eicosenoic acid); all-cis-5,8,11-eicosatrienoic acid (mead acid); cis-13-docosenoic acid (erucic acid), and cis-15-tetracosenoic acid (nervonic acid). Examples of conjugated fatty acids include 9Z,11E-octadeca-9,11-dienoic acid (rumenic acid); 10E,12Z-octadeca-9,11-dienoic acid; 8E,10E,12Z-octadecatrienoic acid (α-calendic acid); 8E,10E,12E-octadecatrienoic acid (β-Calendic acid); 8E,10Z,12E-octadecatrienoic acid (jacaric acid); 9E,11E,13Z-octadeca-9,11,13-trienoic acid (α-eleostearic acid); 9E,11E,13E-octadeca-9,11,13-trienoic acid (β-eleostearic acid); 9Z,11Z,13E-octadeca-9,11,13-trienoic acid (catalpic acid), and 9E,11Z,13E-octadeca-9,11,13-trienoic acid (punicic acid).

Suitable essential oils include, but are not limited to, peppermint oil, cinnamon leaf oil, lemongrass oil, clove oil, castor oil, wintergreen oil, sweet orange, spearmint oil, ceaderwood oil, aldehyde C16, α-terpineol, amyl cinnamic aldehyde, amyl salicylate, anisic aldehyde, benzyl alcohol, benzyl acetate, camphor, capsaicin, cinnamaldehyde, cinnamic alcohol, carvacrol, carveol, citral, citronellal, citronellol, p-cymene, diethyl phthalate, dimethyl salicylate, dipropylene glycol, eucalyptol (cineole), eugenol, iso-eugenol, galaxolide, geraniol, guaiacol, ionone, listea cubea, menthol, menthyl salicylate, methyl anthranilate, methyl ionone, methyl salicylate, a-phellandrene, pennyroyal oil, perillaldehyde, 1- or 2-phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil, thymol, metabolites of trans-anethole, vanillin, ethyl vanillin, similar compositions, and combinations thereof.

Probiotics and prebiotics may include yeast and bacteria that help establish an immune protective rumen or gut microflora as well as small oligosaccharides. By way of non-limiting example, yeast-derived probiotics and prebiotics include yeast cell wall derived components such as β-glucans, arabinoxylan isomaltose, agarooligosaccharides, lactosucrose, cyclodextrins, lactose, fructooligosaccharides, laminariheptaose, lactulose, β-galactooligosaccharides, mannanoligosaccharides, raffinose, stachyose, oligofructose, glucosyl sucrose, sucrose thermal oligosaccharide, isomaltrose, caramel, inulin, and xylooligosaccharides. In an exemplary embodiment, the yeast-derived agent may be β-glucans and/or mannanoligosaccharides. Sources for yeast cell wall derived components include *Saccharomyces bisporus, Saccharomyces boulardii, Saccharomyces cerevisiae, Saccharomyces capsularis, Saccharomyces delbrueckii, Saccharomyces fermentati, Saccharomyces lugwigii, Saccharomyces microellipsoides, Saccharomyces pastorianus, Saccharomyces rosei, Candida albicans, Candida cloaceae, Candida tropicalis, Candida utilis, Geotrichum candidum, Hansenula americana, Hansenula anomala, Hansenula wingei,* and *Aspergillus oryzae.*

Probiotics and prebiotics may also include bacteria cell wall derived agents such as peptidoglycan and other components derived from gram-positive bacteria with a high content of peptidoglycan. Exemplary gram-positive bacteria include *Lactobacillus acidophilus, Bifedobact thermophilum, Bifedobat longhum, Streptococcus faecium, Bacillus pumilus, Bacillus subtilis, Bacillus licheniformis, Lactobacillus acidophilus, Lactobacillus casei, Enterococcus faecium, Bifidobacterium bifidium, Propionibacterium acidipropionici, Propionibacteriium freudenreichii,* and *Bifidobacterium pseudolongum.*

The bioactive may be an amino acid or amino acid analogue. Non-limiting suitable amino acids alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, or other known amino acids. Amino acid analogs include α-hydroxy analogs, as well side chain protected analogs or N-derivatized amino acids including 2-hydroxy-4-methylthiobutanoic acid or its corresponding salt. In one embodiment, the bioactive is the calcium salt of 2-hydroxy-4-methylthiobutanoic acid.

The bioactive may also be an enzyme. As used herein, variants are understood to be included in the term enzyme. Suitable non-limiting examples of enzymes include amylases, carbohydrases, cellulases, esterases, galactonases, galactosidases, glucanases, hemicellulases, hydrolases, lipases, oxidoreductases, pectinases, peptidases, phosphatases, phospholipases, phytases, proteases, transferases, xylanases, and combinations thereof.

Suitable herbals and herbal derivatives, as used herein, refer to herbal extracts, and substances derived from plants and plant parts, such as leaves, flowers and roots, without limitation. Non-limiting exemplary herbals and herbal derivatives include agrimony, alfalfa, aloe vera, amaranth, angelica, anise, barberry, basil, bayberry, bee pollen, birch, bistort, blackberry, black cohosh, black walnut, blessed thistle, blue cohosh, blue vervain, boneset, borage, buchu, buckthorn, bugleweed, burdock, capsicum, cayenne, caraway, cascara sagrada, catnip, celery, centaury, chamomile, chaparral, chickweed, chicory, chinchona, cloves, coltsfoot, comfrey, cornsilk, couch grass, cramp bark, culver's root, cyani, cornflower, damiana, dandelion, devils claw, dong quai, echinacea, elecampane, ephedra, eucalyptus, evening primrose, eyebright, false unicorn, fennel, fenugreek, figwort, flaxseed, garlic, gentian, ginger, ginseng, golden seal, gotu kola, gum weed, hawthorn, hops, horehound, horseradish, horsetail, hoshouwu, hydrangea, hyssop, iceland moss, irish moss, jojoba, juniper, kelp, lady's slipper, lemon grass, licorice, lobelia, mandrake, marigold, marjoram, marshmallow, mistletoe, mullein, mustard, myrrh, nettle, oatstraw, oregon grape, papaya, parsley, passion flower, peach, pennyroyal, peppermint, periwinkle, plantain, pleurisy root, pokeweed, prickly ash, psyllium, quassia, queen of the meadow, red clover, red raspberry, redmond clay, rhubarb, rose hips, rosemary, rue, safflower, saffron, sage, St. John's wort, sarsaparilla, sassafras, saw palmetto, scullcap, senega, senna, shepherd's purse, slippery elm, spearmint, spikenard, squawvine, stillingia, strawberry, taheebo, thyme, uva ursi, valerian, violet, watercress, white oak bark, white pine bark, wild cherry, wild lettuce, wild yam, willow, wintergreen, witch hazel, wood betony, wormwood, yarrow, yellow dock, yerba santa, yucca and combinations thereof.

Suitable non-limiting pigments include actinioerythrin, alizarin, alloxanthin, β-apo-2'-carotenal, apo-2-lycopenal, apo-6'-lycopenal, astacein, astaxanthin, azafrinaldehyde, aacteriorubenin, aixin, α-carotine, β-carotine, γ-carotine, β-carotenone, canthaxanthin, capsanthin, capsorubin, citranaxanthin, citroxanthin, crocetin, crocetinsemialdehyde, crocin, crustaxanthin, cryptocapsin, α-cryptoxanthin, β-cryptoxanthin, cryptomonaxanthin, cynthiaxanthin, decaprenoxanthin, dehydroadonirubin, diadinoxanthin, 1,4-diamino-2,3-dihydroanthraquinone, 1,4-dihydroxyanthraquinone, 2,2'-Diketospirilloxanthin, eschscholtzxanthin, eschscholtzxanthone, flexixanthin, foliachrome, fucoxanthin, gazaniaxanthin, hexahydrolycopene, hopkinsiaxanthin, hydroxyspheriodenone, isofucoxanthin, loroxanthin, lutein, luteoxanthin, lycopene, lycopersene, lycoxanthin, morindone, mutatoxanthin, neochrome, neoxanthin, nonaprenoxanthin, OH-Chlorobactene, okenone, oscillaxanthin, paracentrone, pectenolone, pectenoxanthin, peridinin, phleixanthophyll, phoeniconone, phoenicopterone, phoenicoxanthin, physalien, phytofluene, pyrrhoxanthininol, quinones, rhodopin, rhodopinal, rhodopinol, rhodovibrin, rhodoxanthin, rubixanthone, saproxanthin, semi-α-carotenone, semi-β-carotenone, sintaxanthin, siphonaxanthin, siphonein, spheroidene, tangeraxanthin, torularhodin, torularhodin methyl ester, torularhodinaldehyde, torulene, 1,2,4-trihydroxyanthraquinone, triphasiaxanthin, trollichrome, vaucheriaxanthin, violaxanthin, wamingone, xanthin, zeaxanthin, α-zeacarotene and combinations thereof.

Suitable non-limiting pharmaceutically acceptable agents include an acid/alkaline-labile drug, a pH dependent drug, or a drug that is a weak acid or a weak base. Examples of acid-labile drugs include statins (e.g., pravastatin, fluvastatin and atorvastatin), antibiotics (e.g., penicillin G, ampicillin, streptomycin, erythromycin, clarithromycin and azithromycin), nucleoside analogs [e.g., dideoxyinosine (ddI or didanosine), dideoxyadenosine (ddA), dideoxycytosine (ddC)], salicylates (e.g, aspirin), digoxin, bupropion, pancreatin, midazolam, and methadone. Drugs that are only soluble at acid pH include nifedipine, emonapride, nicardipine, amosulalol, noscapine, propafenone, quinine, dipyridamole, josamycin, dilevalol, labetalol, enisoprost, and metronidazole. Drugs that are weak acids include phenobarbital, phenytoin, zidovudine (AZT), salicylates (e.g., aspirin), propionic acid compounds (e.g., ibuprofen), indole derivatives (e.g., indomethacin), fenamate compounds (e.g., meclofenamic acid), pyrrolealkanoic acid compounds (e.g., tolmetin), cephalosporins (e.g., cephalothin, cephalaxin, cefazolin, cephradine, cephapirin, cefamandole, and cefoxitin), 6-fluoroquinolones, and prostaglandins. Drugs that are weak bases include adrenergic agents (e.g., ephedrine, desoxyephedrine, phenylephrine, epinephrine, salbutamol, and terbutaline), cholinergic agents (e.g., physostigmine and neostigmine), antispasmodic agents (e.g., atropine, methantheline, and papaverine), curariform agents (e.g., chlorisondamine), tranquilizers and muscle relaxants (e.g., fluphenazine, thioridazine, trifluoperazine, chlorpromazine, and triflupromazine), antidepressants (e.g., amitriptyline and nortriptyline), antihistamines (e.g., diphenhydramine, chlorpheniramine, dimenhydrinate, tripelennamine, perphenazine, chlorprophenazine, and chlorprophenpyridamine), cardioactive agents (e.g., verapamil, diltiazem, gallapomil, cinnarizine, propranolol, metoprolol and nadolol), antimalarials (e.g., chloroquine), analgesics (e.g., propoxyphene and meperidine), antifungal agents (e.g., ketoconazole and itraconazole), antimicrobial agents (e.g., cefpodoxime, proxetil, and enoxacin), caffeine, theophylline, and morphine. In another embodiment, the drug may be a biphosphonate or another drug used to treat osteoporosis. Non-limiting examples of a biphosphonate include alendronate, ibandronate, risedronate, zoledronate, pamidronate, neridronate, olpadronate, etidronate, clodronate, and tiludronate. Other suitable drugs include estrogen, selective estrogen receptor modulators (SERMs), and parathyroid hormone (PTH) drugs. In yet another embodiment, the drug may be an antibacterial agent. Suitable antibiotics include aminoglycosides (e.g., amikacin, gentamicin, kanamycin, neomycin, netilmicin, streptomycin, and tobramycin), carbecephems (e.g., loracarbef) a carbapenem (e.g., certapenem, imipenem, and meropenem), cephalosporins (e.g., cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone), macrolides (e.g., azithromycin, clarithromycin, dirithromycin, erythromycin, and troleandomycin), monobactam, penicillins (e.g., amoxicillin, ampicillin, carbenicillin, cloxacillin, dicloxacillin, nafcillin, oxacillin, penicillin G, penicillin V, piperacillin, and ticarcillin), polypeptides (e.g., bacitracin, colistin, and polymyxin B), quinolones (e.g., ciprofloxacin, enoxacin, gatifloxacin, levofloxacin, lomefloxacin, moxifloxacin, norfloxacin, ofloxacin, and trovafloxacin), sulfonamides (e.g., mafenide, sulfacetamide, sulfamethizole, sulfasalazine, sulfisoxazole, and trimethoprim-sulfamethoxazole), and tetracyclines (e.g., demeclocycline, doxycycline, minocycline, and oxytetracycline). In an alternate embodiment, the drug may be an antiviral protease inhibitor (e.g., amprenavir, fosamprenavir, indinavir, lopinavir/ritonavir, ritonavir, saquinavir, and nelfinavir). In a still another embodiment, the drug may be a cardiovascular drug. Examples of suitable cardiovascular agents include cardiotonic agents (e.g., digitalis (digoxin), ubidecarenone, and dopamine), vasodilating agents (e.g., nitroglycerin, captopril, dihydralazine, diltiazem, and isosorbide dinitrate), antihypertensive agents (e.g., alpha-methyldopa, chlortalidone, reserpine, syrosingopine, rescinnamine, prazosin, phentolamine, felodipine, propanolol, pindolol, labetalol, clonidine, captopril, enalapril, and lisonopril), beta blockers (e.g., levobunolol, pindolol, timolol maleate, bisoprolol, carvedilol, and butoxamine), alpha blockers (e.g., doxazosin, prazosin, phenoxybenzamine, phentolamine, tamsulosin, alfuzosin, and terazosin), calcium channel blockers (e.g., amlodipine, felodipine, nicardipine, nifedipine, nimodipine, nisoldipine, nitrendipine, lacidipine, lercanidipine, verapamil, gallopamil, and diltiazem), and anticlot agents (e.g., dipyrimadole).

The bioactive can be in any form including in a solid, a gel, an emulsion, or any combination thereof. A solid, as used herein, can include a granule, a powder, or a crystal. In such cases, the bioactive core may range in size from about 0.001 millimeters to 10 millimeters. In some embodiments, the bioactives are about 0.1 millimeters to 5 millimeters. In a preferred embodiment, the bioactives are about 0.1 millimeters to 3 millimeters.

(c). Composition

The composition comprising a layer formed over a core may be in a variety of configurations. The core may be in any shape including rods, spheroids, cylinders, and the like. Generally, the layer comprising the first polymer is formed over the core such as to completely surround the core. In some embodiments, the core may be in direct contact with the layer comprising the first polymer, and in other embodiments, one or more additional layers are formed between the core and the layer comprising the first polymer. In alternate embodiments, one or more additional layers are formed over the layer comprising the first polymer.

In some embodiments, the composition comprises an additional layer substantially that is hydrophobic. The hydrophobic layer may be comprised of a hydrophobic agent. Hydrophobic agents are generally those with a contact angle above 90°. In some embodiments, the hydrophobic layer is comprised of a wax, a polymer, or a fatty acid, including $C_{12}$-$C_{30}$ fatty acids, or a fatty acid ester, including monoglycerides, diglycerides, and triglycerides. In some embodiments, the hydrophobic layer is chosen from canola oil, coconut oil, corn oil, cottonseed oil, lauric acid, linoleic acid, oleic acid, palm oil, palmitic acid, soy oil, soybean oil, stearic acid, stearin, sunflower seed oil, vegetable oil, or the hydrogenated forms of any of these, and combinations thereof.

In some embodiments, the composition comprises an additional layer that is substantially hydrophilic. The hydrophilic layer is comprised of water soluble molecules and dissolves in water. In preferred embodiments, the hydrophilic layer is chosen from hydroxymethylcellulose, hydroxypropylcellulose, methylcellulose, ethylcellulose, carboxymethyl cellulose, and combinations thereof.

In one embodiment, the additional layer is a mixture of a non-reactive wax and a carbonate as described in section (VI).

The additional layer(s) can be provided in a variety of thicknesses around the core or layer. The amount of material comprising the additional layer may range from about 1% to about 75% of the total weight of the composition (core and layer(s)). In other embodiments, the amount of material comprising the additional layer may range from about 1% to about 50% of the total weight of the composition. In various embodiments, the amount of material comprising the layer is about 1% to about 10%, about 5% to about 15%, about 10% to about 20%, about 15% to about 25%, about 20% to about 30%, about 25% to about 35%, about 30% to about 40%, about 35% to about 45%, or about 40% to about 50% of the total weight of the composition. In particular embodiments, the additional layer is about 5%, about 10%, about 15%, or about 20% of the total weight of the composition.

A variety of commonly used excipients in pharmaceutical and nutritive formulations may be utilized with any bioactives described above. Non-limiting examples of suitable excipients include an agent selected from the group consisting of non-effervescent disintegrants, a coloring agent, a flavor-modifying agent, an oral dispersing agent, a stabilizer, a preservative, a diluent, a compaction agent, a lubricant, a filler, a binder, taste masking agents, an effervescent disintegration agent, and combinations of any of these agents. In some embodiments, the additional layer may further comprise a polymer having a repeat unit of Formula (I).

In one embodiment, the excipient may be a disintegrant or a superdisintegrant. Suitable disintegrants include, without limit, starches (such as corn starch, potato starch, and the like), pregelatinized and modified starches thereof, microcrystalline cellulose (including, but not limited to ethyl cellulose, methyl cellulose or combinations thereof), alginates, sodium starch glycolate, and gums (such as agar, guar, locust bean, karaya, pectin, and tragacanth). Non-limiting examples of suitable superdisintegrants include crospovidine, sodium carboxymethylcellulose, croscarmellose sodium, sodium starch glycolate, low substituted hydroxypropyl cellulose, and sodium bicarbonate. In one preferred embodiment, the composition may comprise sodium carboxymethylcellulose as a superdisintegrant.

(d). Properties

The compositions comprising the layer comprising a first polymer may have improved physical properties including pH switch properties, improved release profiles for the bioactive, and improved mechanical properties.

The layer comprising the first polymer may have a pH switch effect where the compositions are stable in an aqueous solution under approximately neutral pH, but hydrolyze at a lower pH. For example, the layer comprising the first polymer is stable at a pH of about 6.0, about 6.5, about 7.0, and about 7.5. The compositions comprising the first polymer hydrolyze in an aqueous solution having a pH of less than about pH 5.0.

Hydrolysis of the composition results in release of the bioactive from the composition comprising the first layer. Accordingly, the compositions may be used to achieve a particular release profile for the bioactive agent.

At an approximately neutral pH, the compositions may be characterized by minimal release of the bioactive. In one embodiment, a minimal release profile may show a release profile substantially similar to the pH 6.5 release profiles shown in FIG. 1, 2, 3, 4, 6, 8, or 9. In another embodiment, at an approximately neutral pH, release is characterized by less than 20% of the total bioactive being released from the composition. In still other embodiments, a minimum release is characterized by less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of the total bioactive in the composition being released.

At a pH of less than 5.0, the compositions may have a release profile for the bioactive which is substantially constant, first-order, sigmoidal, or delayed. Generally, the release rate at a pH of less than 5.0 is higher than the release rate at approximately neutral conditions. In some embodiments, the compositions have a release profile that is substantially similar to the release profiles at pH 2.5 release profiles shown in FIG. 1, 2, 3, 6, 8, or 9. In one preferred embodiment, release at a pH of less than 5.0 is substantially constant. A substantially constant release refers to release of a bioactive that is constant over a period of time, for example, varying by less than 1%, less than 0.5%, or 0.25% in different embodiments. The compositions may show a constant release rate at a pH below about 5.0 for a period of 1 to 24 hours. In some embodiments, the release rate is constant over a period of about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. Depending on the time period and pH, the release of the bioactive may range from less than 1% per hour to more than 30% per hour. The release profile is tunable based on the amount of the first polymer in the layer. Higher percentages of the first polymer in the layer correspond to a higher percentage of bioactive released per hour, while lower amounts of the first polymer correspond to a lower percentage release per hour.

In still another embodiment, the release profile may show an initial high rate of release at a pH of less than 5.0. In such embodiments, the release rates at a pH of 5.0 or lower may be greater over the first 1 to 5 hours at a pH of 5.0 or lower. In some embodiments, this initial period of rapid release of bioactive is followed by a period of constant release.

The compositions of the invention have improved durability, plasticity, and mechanical properties. Such properties are advantageous for compositions that may be subject to mastication (i.e. in the context of providing the composition to an animal) or in the context of mechanical stresses of industrial processing such as mixing and conveying equipment. Resiliency of the compositions against mechanical force can be measured by the impact test described in Example 8. In some embodiments, the compositions of the invention release less than 10% of the total bioactive when subjected to 25 impacts. In other embodiments, the compositions of the invention release less than 9%, or less than 8% or less than 7%, or less than 6% or less than 5%, or less than 4%, or less than 3%, or less than 2% or less than 1% of the bioactive when subjected to 25 impacts.

II. Matrix Composition

The disclosure also provides an agglomerated composition comprising a plurality of bioactive agents embedded in a matrix. The matrix comprises a first polymer comprising a repeat unit of Formula (I).

(a). Agglomerated Composition

The agglomerated composition comprises a plurality of bioactive agents embedded in a matrix. The matrix comprises a first polymer comprising a repeat unit of Formula (I). The first polymer is described in section (I)(a). Suitable bioactive agents for use in the matrix are described in section (I)(b)(i).

The agglomerated composition comprises a plurality of bioactive agents embedded in a matrix. The agglomerated composition formed by the matrix and bioactive agents can be in any shape including rods, spheroids, cylinders, and the like. Additionally, the agglomerated composition can be shaped for a particular need. For, example, the agglomerated composition can be shaped to cap open ends of a cylinder.

The bioactive can be present in the agglomerated composition in a weight of about 20% to about 90% of the total composition. In some embodiments the bioactive is about 10%, about 15%, about 20%, about 25%, about 30%, about 35%, about 40%, about 45%, about 50%, about 55%, about 60%, about 65%, about 70%, about 80%, about 90%, or about 99% by weight of the total composition. In a preferred embodiment, the bioactive is present in an amount of about 80% to about 90%, or 85% to about 95%, or about 95% to about 99% by weight of the total composition.

The bioactive agents may be embedded in the matrix in a variety of ways depending on the shape and intended use of the agglomerated composition. In some embodiments, the bioactive agents are homogeneously dispersed in the matrix composition, meaning that the bioactive is provided in approximately the same concentration throughout the matrix. In other embodiments, the bioactive agents may be more or less concentrated in certain parts of the matrix. When one or more bioactive agents are in the matrix, they may either be dispersed approximately homogeneously, or ordered within the matrix. For example, in embodiments where more than one bioactive is present, the bioactives may be laterally separated in the composition. In other embodiments, the bioactives may be more highly concentrated in the inner portion of the matrix than at the outer surface of the matrix.

The agglomerated composition may comprise at least one additional agent in the matrix. The additional agent may be chosen from polymers, including crystalline and semi-crystalline polymers. Examples of suitable polymers, without limitation, are polymers of acrylates, aminoacrylates, alkylene succinates, alkylene oxalates, amides, amino acids, anhydrides, arylates, carbonates, cellulose (including, but not limited to ethyl cellulose, methyl cellulose or combinations thereof), caprolactone, cyanoacrylates, dihydropyrans, dioxanes, dioxanones, ether ether ketones, ethylene glycol, fumarates, hydroxyalkanoates, hydroxyl-esters, imides, ketals, lactides, methacrylates, methyl olefins, orthoesters, phosphazines, styrenes, terephthalates, trimethylene carbonate, urathanes, vinyl acetates, vinyl ketones, vinyl halides, derivatives, isomers, and mixtures thereof. In some embodiments, the additional agent may be chosen from polyacrylamide, polystyrene, polyvinylpyrrolidone, polyvinylacetate. The additional agent may also be a wax, including natural and synthetic waxes, fatty acids, including $C_{12}$-$C_{30}$ fatty acids, and fatty acid esters including monoglycerides, diglycerides, and triglycerides and hydrogenated fatty acid esters, non-limiting examples include canola oil, coconut oil, corn oil, cottonseed oil, lauric acid, linoleic acid, oleic acid, palm oil, palmitic acid, soy oil, soybean oil, stearic acid, stearin, sunflower seed oil, vegetable oil, and combinations thereof. The oils may be hydrogenated, non-hydrogenated or partially hydrogenated. The additional agent may also be a flow agent such as a carbonate, talc, magnesium stearate and the like. Carbonates may be selected from copper carbonate, zinc carbonate, calcium carbonate, magnesium carbonate, potassium carbonate, sodium carbonate, and combinations thereof. The additional agent may also be a bicarbonate, including potassium bicarbonate or another alkali metal bicarbonate. In a preferred embodiment, the additional agent is a cellulose polymer selected from hydroxymethylcellulose, hydroxyproplycellulose, methylcellulose, carboxymethyl cellulose and ethylcellulose. The additional agent may be a salt of an above listed compound including alkali metal salts such as calcium, magnesium, potassium, sodium, lithium and the like.

In one embodiment, the additional agent is a pH-sensitive polymer and may be chosen from natural and modified polymers (e.g. chitosan) including blends with monomers. The additional agents may be amino type polymers. Amino type polymers include, but are not limited to, pyridine, pyridine derivatives, amino acrylate type monomers, such as dialkylamino ethyl acrylate, styrene, styrene derivatives (such as poly-2-vinylpyridine-co-styrene), acrylonitrile, acrylate type monomers of acrylic acid, vinyl esters, vinyl acetate, and vinyl substituted heterocyclic rings that contain nitrogen fusions (such as vinyl carbazole, vinyl quinolone and N-vinylpyrrole). In one preferred embodiment, the additional agent is poly-2-vinylpyridine-co-styrene.

In one alternative embodiment, the agglomerated composition is free from ethylcellulose.

In some embodiments, the first polymer is about 5% to about 50% by weight of the matrix and the additional agent comprises from about 50% to about 95% by weight of the matrix. In various embodiments, the additional agent(s) comprise about 50%, about 60%, about 70%, about 80%, or about 90% of the matrix. In various embodiments, where two or more additional agents are present with the first polymer in the matrix, the additional agents can be present in any ratio without limitation.

(b). Optional Layers

In some embodiments, the matrix composition may be coated by at least one layer. The layer may be as described in section (I), or substantially hydrophilic or substantially hydrophobic. As will be understood by the skilled artisan, different layers can be combined and layered on the agglomerated composition.

In some embodiments, the layer is substantially hydrophobic. The hydrophobic layer may be comprised of a hydrophobic agent. Hydrophobic agents are generally those with a contact angle above 90°. In some embodiments, the hydrophobic layer is comprised of a wax, a polymer, a fatty acid including $C_{12}$-$C_{30}$ fatty acids, or fatty acid esters, including monoglycerides, diglycerides, and triglycerides. Non-limiting examples include canola oil, coconut oil, corn oil, cottonseed oil, lauric acid, linoleic acid, oleic acid, palm oil, palmitic acid, soy oil, stearic acid, stearin, sunflower seed oil, vegetable oil, and combinations thereof. The oils may be hydrogenated, non-hydrogenated, or partially hydrogenated.

In various embodiments, the layer is substantially hydrophilic. A hydrophilic layer, in contrast to a hydrophobic layer, comprises hydrophilic components. In preferred embodiments, the hydrophilic layer is chosen from hydroxymethylcellulose, hydroxyproplycellulose, methylcellulose, ethylcellulose, carboxymethyl cellulose, and combinations thereof.

A variety of commonly used excipients in pharmaceutical and nutritive formulations may be utilized with any such agents described above. Non-limiting examples of suitable excipients include an agent selected from the group consisting of non-effervescent disintegrants, a coloring agent, a flavor-modifying agent, an oral dispersing agent, a stabilizer, a preservative, a diluent, a compaction agent, a lubricant, a filler, a binder, taste masking agents, an effervescent disintegration agent, and combinations of any of these agents.

The matrix comprising the first polymer may also have a pH switch effect where the compositions are stable in an aqueous solution under approximately neutral pH, but hydrolyze at a lower pH. For example, the matrix comprising the first polymer is stable at a pH level of about 6.0, about 6.5, about 7.0, and about 7.5, but the matrix comprising the first polymer hydrolyzes in an aqueous solution having a pH of less than about pH 5.0.

Hydrolysis of the composition results in release of the bioactive from the composition comprising the first layer. Accordingly, the compositions may be used to achieve a particular release profile for the bioactive agent.

At an approximately neutral pH, the compositions may be characterized by minimal release of the bioactive. In one embodiment, a minimal release may show a release profile substantially similar to the pH 6.5 release profiles shown in FIG. 1, 2, 3, 4, 5, 6, 8, or 9. In another embodiment, at an approximately neutral pH, release is characterized by less than 20% of the total bioactive being released from the composition. In still other embodiments, a minimum release is characterized by less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of the total bioactive in the composition.

At a pH of less than 5.0, the compositions may have a release profile which is substantially constant, first-order, sigmoidal, or delayed. Generally, the release rate at a pH of less than 5.0 is higher than the release rate at approximately neutral conditions. In some embodiments, the compositions have a release profile that is substantially similar to the release profiles at pH 2.5 release profiles shown in FIG. 1, 2, 3, 5, 6, 8, or 9. In one preferred embodiment, release at a pH of less than 5.0 is substantially constant. A substantially constant release refers to release of a bioactive that is constant over a period of time. The compositions may show a constant release rate at a pH below 5.0 for a period of 1 to 24 hours. In some embodiments, the release rate is constant over a period of about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. Depending on the time period and pH, the release of the bioactive may range from less than 1% per hour to more than 30% per hour. In one embodiment, the composition has a constant release rate of about 10% of the bioactive per hour at a pH of 2.5.

In still another embodiment, the release profile may show an initial high rate of release at a pH of less than 5.0. In such embodiments, the release rates at a pH of 5.0 or lower may be greater over the first 1 to 5 hours at a pH of 5.0 or lower. In some embodiments, this initial period of rapid release of bioactive is followed by a period of constant release.

The compositions of the invention have improved durability, plasticity, and mechanical properties. Such properties are advantageous for compositions that may be subject to mastication (i.e. in the context of providing the composition to an animal) or in the context of mechanical stresses of industrial processing such as mixing and conveying equipment. Resiliency of the compositions against mechanical force can be measured by the impact test described in Example 8. In some embodiments, the compositions of the invention release less than 10% of the total bioactive when subjected to 25 weight impacts. In other embodiments, the compositions of the invention release less than 9%, or less than 8% or less than 7%, or less than 6% or less than 5%, or less than 4%, or less than 3%, or less than 2% or less than 1% of the bioactive when subjected to 25 weight impacts.

III. Food Composition

A further aspect of the disclosure provides a food composition comprising (i) a nutritive source and (ii) a composition comprising at least one bioactive agent and a polymer having a repeat unity of Formula (I) as detailed above in sections (I) and (II). The nutritive source may be a carbohydrate source, a protein source, a fat source, or combinations thereof. In some aspects, the nutritive source is provided by the layer or matrix composition. The food composition may be formulated as a liquid, dry pellet, powder, or emulsion.

A variety of carbohydrate sources may be included as the nutritive source in the food composition. The carbohydrate source may be of plant, microbial, or animal origin. Examples of suitable plant sources of carbohydrates include, without limit, grains such as wheat, oats, rice, rye, and so forth; legumes such as soy, peas, beans, and the like; corn; grasses; potatoes; vegetable plants; and plant fruits. The carbohydrate may be a monosaccharide such as pentose, glucose, galactose, and so forth; a disaccharide such as sucrose, lactose, maltose, and the like; an oligosaccharide such as a fructo-oligosaccharide, galactose-oligosaccharide, mannan-oligosaccharide, etc.; or a polysaccharide such as starch, glycogen, cellulose, arabinoxylan, pectin, gum, chitins, and so forth.

Numerous protein sources may be included in the food composition. The protein source may be derived from a plant. Non-limiting examples of suitable plants that provide a good source of protein include amaranth, arrowroot, barley, buckwheat, canola, cassava, channa (garbanzo), legumes, lentils, lupin, maize, millet, oat, pea, potato, rice, rye, sorghum, soybean, sunflower, tapioca, triticale, wheat, seagrasses, and algae. Alternatively, the protein source maybe derived from an animal. For example, the animal protein source may be derived from a dairy product, bird eggs, or from the muscles, organs, connective tissues, or skeletons of land-based or aquatic animals.

A variety of fat sources are suitable for use as the nutritive source in the food composition. The fat source may be of plant, animal, or microbial origin. Non-limiting examples of plant derived fats include vegetable oils (e.g., canola oil, corn oil, cottonseed oil, palm oil, peanut oil, safflower oil, soybean oil, and sunflower oil) and oilseeds (e.g., canola seeds, cottonseeds, flax seeds, linseeds, Niger seeds, sesame seeds, soy beans, and sunflower seeds), distillers grains, or algae. Animal derived fats include, without limit, fish oils (e.g., menhaden oil, anchovy oil, albacore tuna oil, cod liver oil, herring oil, lake trout oil, mackerel oil, salmon oil, and sardine oil), high fat fish meal (e.g., menhaden meal, anchovy meal, herring meal, pollack meal, salmon meal, tuna meal, and whitefish meal), and animal fats (e.g., poultry fat, beef tallow, butter, pork lard, and whale blubber).

The amount of nutritive agent present in the food composition can and will vary depending upon the ingredients present in the food composition and its intended use. In general, the amount of nutritive source present in the food composition may range from about 1% to about 99% by weight of the food composition. In various embodiments, the amount of nutritive source present in the food composition may range from about 1% to about 3%, from about 3% to about 10%, from about 10% to about 30%, or from about 30% to about 99% by weight of the food composition. Similarly, the amount of the composition detailed in sections (I) or (II) present in the food composition can and will vary. In certain embodiments, the amount of a composition comprising at least one bioactive agent and a polymer having a repeat unity of Formula (I) present in the food composition may range from about 1% to about 3%, from about 3% to about 10%, from about 10% to about 30%, or from about 30% to about 99% by weight of the food composition.

In some aspects, a nutritive is provided by the hydrolysis product of the first polymer comprising Formula (I). In some embodiments the polymer is not available as a nutritive agent until it is hydrolyzed from the first polymer. In one preferred embodiment, the nutritive agent is a methionine source, preferably 2-hydroxy-4-methylthiobutanoic acid IV. Method for Providing a Bioactive Agent to a Subject Still another aspect of the present disclosure encompasses a method from providing at least one bioactive agent to a subject. The method comprises administering to the subject a composition comprising the bioactive agent, wherein the composition comprising the bioactive agent is detailed above in sections (I)-(III).

The composition comprising the bioactive agent may be administered by variety of routes such as, e.g., oral, transmucosal, topical, or parenteral. A preferred route of administration is oral. The composition may be administered to the subject as a particulate, as solid dosage form (e.g., tablet, caplet, capsule, etc.), as a liquid, or as a powder or granulate. The composition may be administered once a week, several times a week, once a day, or two or more times a day.

The composition may be administered to a variety of subjects. Suitable subjects include humans, food animals, companion animals, research animals, and zoo animals. Non-limiting examples of food animals include ruminants (e.g., beef cattle, dairy cows, sheep, goats, and bison) and monogastrics (e.g., pigs and avian such as chickens, ducks, emu, game hens, geese, guinea fowl/hens, quail, ostriches, and turkeys). Additional monogastric species include aquatic species (e.g., fish and crustaceans including, but not limited to, salmon, shrimp, carp, tilapia and shell fish). Suitable companion animals include, but are not limited to, cats, dogs, horses, rabbits, rodents (e.g., mice, rats, hamsters, gerbils, and guinea pigs), hedgehogs, and ferrets. Examples of research animals include rodents, cats, dogs, rabbits, pigs, and non-human primates. Non-limiting examples of suitable zoo animals include non-human primates, lions, tigers, bears, elephants, giraffes, and the like. In a preferred embodiment the subject is a ruminant. Non-limiting examples of ruminants include cattle, sheep, goats, bison, deer, moose, elk, reindeer, caribou, camels, giraffes, antelope, and llama.

The layer or matrix composition having a repeat unit comprising Formula (I) is stable in an aqueous solution under approximately neutral pH. For example, the composition is stable at a pH level of about 6.0, about 6.5, about 7.0, and about 7.5. The composition comprising the bioactive agent hydrolyzes in an aqueous solution having a pH of less than about pH 5.0. Hydrolysis of the layer or matrix composition releases the bioactive agent. Thus, at pH levels less than about 5.0, the composition undergoes hydrolysis and releases the bioactive agent.

In embodiments in which the subject is a ruminant, therefore, the composition remains stable and is not degraded during the time in which the composition is in the rumen of the subject. Upon entry into abomasum, in which the pH is low, the composition hydrolyzes and releases the bioactive agent. Accordingly, the compositions may be used for rumen bypass as the bioactives are protected by the unhydrolyzed matrix composition and are selectively released in the low pH environment of the abomasum.

V. Methods of Making Matrix and Layer Compositions

The processes used to form the layer and matrix compositions can and preferably will vary. By way of non-limiting example, the desired amount of the first polymer, the bioactive, and any additional agents are combined. In various aspects the agents may be combined in the presence of water or an organic solvent, such as methanol or ethanol. The mixture may be further processed before shaping into a suitable delivery form as described in sections (I) and (II). In some embodiments, ingredients are extruded, granulated, blended, or processed through a hot melt process prior to shaping.

The matrix compositions may be shaped in any way including manually or by a press or die. The layers of the invention may be formed over a core by methods generally known in the art, such as by dry powder layering, hand applying, by or by a fluid bed process, for example using a solvent or a hot melt. Detailed information concerning materials, equipment and processes for preparing and applying an outer layer over in inner core may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, 6$^{th}$ Ed. (Media, Pa.: Williams & Wilkins, 1995).

VI. Layer Compositions Comprising a Compound of Formula (V)

In still another aspect, the present disclosure provides a layer composition comprising the compound of Formula (V). The composition comprising the layer is formed over a core, the core comprising a bioactive agent and the layer comprising non-reactive fatty acid ester and a carbonate. The core may be any core as described in section (I)(b). Suitable bioactive agents include those described in section (I)(b)(i).

The layer comprises a polymer having a repeat unit of Formula (V):

wherein,
    $R^2$ is $CH_3$;
    $R^3$ is chosen from hydrogen, hydrocarbyl, and substituted hydrocarbyl;
    n is zero; and
    m is an integer >1.

$R^3$ can be chosen from hydrogen, hydrocarbyl and substituted hydrocarbyl. In one embodiment, $R^3$ is an alkyl having 1 to 6 hydrocarbons. In a preferred embodiment, $R^3$ is hydrogen.

The molecular weight can and will vary in different embodiments. The molecular weight can range between 1,000 Da and about 200,000 Da. In various embodiments, the molecular weight of the polymer is about 2,000, 10,000, 20,000 Da, 30,000 Da, 40,000 Da, 50,000 Da, 60,000 Da, 70,000 Da, 80,000 Da, 90,000 KDa, 100,000 Da, or a number between any two of these values. The weight of a mixture of polymers may be characterized by its mass-average molecular weight. In some aspects, the mass-average molecular weight of the polymers may be at least 500 KDa. In other aspects, the mass average molecular weight ranges from about 1,000 Da to about 100,000 Da.

In some aspects of the invention, Formula (V) may have chiral centers. In particular, the carbon alpha to the carbonyl unit in the compound of Formula (I), (II), or (III) may be chiral and may have an R or an S configuration. In some embodiments, the configuration at this position may be R. In other embodiments, the configuration at this position may be S. In various aspects, the repeat units may be all R, all S, or comprise a combination of R and S repeat units, for example, the configuration of the repeat units may alternate in block or randomly.

The layer may further comprise another polymer. Suitable polymers may include crystalline and semi-crystalline polymers. Examples of suitable polymers, without limitation, are polymers of acrylates, aminoacrylates, alkylene succinates, alkylene oxalates, amides, amino acids, anhydrides, arylates, carbonates, cellulose (including, but not limited to, hydroxymethylcellulose, hydroxyproplycellulose, methylcellulose, carboxymethyl cellulose and ethylcellulose), caprolactone, cyanoacrylates, dihydropyrans, dioxanes, dioxanones, ether ether ketones, ethylene glycol, fumarates, hydroxyalkanoates, hydroxyl-esters, imides, ketals, lactides, methacrylates, methyl olefins, orthoesters, phosphazines, styrenes, terephthalates, trimethylene carbonate, urathanes, vinyl acetates, vinyl ketones, vinyl halides, derivatives, isomers, and mixtures thereof.

In one preferred embodiment, the additional agent is the polymer comprising the repeat unit of Formula (I) as described in section (I)(a). In a particularly preferred embodiment, the polymer is the compound of Formula (III).

The layer comprising the polymer having the repeat unit of Formula (V) is stable in an aqueous solution under approximately neutral pH. For example, the layer is stable at a pH level of about 6.0, about 6.5, about 7.0, and about 7.5. The layer hydrolyzes in an aqueous solution having a pH of less than about pH 5.0. Hydrolysis of the layer releases the bioactive agent. Thus, at pH levels from about pH 1.0 to about pH 4.5, the layer undergoes hydrolysis and releases the bioactive agent.

In embodiments in which the subject is a ruminant, therefore, the layer remains stable and is not degraded during the time in which the composition is in the rumen of the subject. Upon entry into abomasum, in which the pH is low, the layer hydrolyzes and releases the bioactive agent. In a preferred embodiment, the bioactive agent is 2-hydroxy-4-methylthiobutanoic acid (HMTBa).

VII. Agglomerated Compositions Comprising a Compound of Formula (V)

In another aspect, the present disclosure provides an agglomerated composition comprising a plurality of bioactive agents embedded in a matrix. The matrix comprises the compound of Formula (V) with the bioactive agents. Suitable bioactive agents for use in the matrix are described in section (I)(a)(i). The composition comprising Formula (V) is described in section (VI).

The agglomerated composition comprises a plurality of bioactive agents embedded in a matrix. The agglomerated composition formed by the matrix and bioactive agents can be in any shape including rods, spheroids, cylinders, and the like. Additionally, the agglomerated composition can be shaped for a particular need. For, example, the agglomerated composition can be shaped to cap open ends of a cylinder.

The bioactive can be present in the agglomerated composition in a weight of about 20% to 80% of the total composition. In some embodiments the bioactive is about 10%, 15%, 20%, 25%, 30%, 35%, 40%, 45%, 50%, 55%, 60%, 65%, 70%, or 80% of the total composition. In a preferred embodiment, the bioactive is present in an amount of about 50 to about 66% of the total agglomerated composition.

The agglomerated composition may further comprise another polymer. Suitable polymers may include crystalline and semi-crystalline polymers. Examples of suitable polymers, without limitation, are polymers of acrylates, aminoacrylates, alkylene succinates, alkylene oxalates, amides, amino acids, anhydrides, arylates, carbonates, cellulose (including, but not limited to, hydroxymethylcellulose, hydroxyproplycellulose, methylcellulose, carboxymethyl cellulose and ethylcellulose), caprolactone, cyanoacrylates, dihydropyrans, dioxanes, dioxanones, ether ether ketones, ethylene glycol, fumarates, hydroxyalkanoates, hydroxyl-esters, imides, ketals, lactides, methacrylates, methyl olefins, orthoesters, phosphazines, styrenes, terephthalates, trimethylene carbonate, urathanes, vinyl acetates, vinyl ketones, vinyl halides, derivatives, isomers, and mixtures thereof.

In one preferred embodiment, the polymer is the compound of comprising the repeat unit of Formula (I) as described in section (I)(a). In a particularly preferred embodiment, the polymer is comprises the repeat unit of Formula (III).

The matrix is stable in an aqueous solution under approximately neutral pH. For example, the matrix is stable at a pH level of about 6.0, about 6.5, about 7.0, and about 7.5. The matrix hydrolyzes in an aqueous solution having a pH of less than about pH 5.0. Hydrolysis of the matrix releases the bioactive agent.

In embodiments in which the subject is a ruminant, therefore, the agglomerated composition remains stable and is not degraded during the time in which the composition is in the rumen of the subject. Upon entry into abomasum, in which the pH is low, the matrix hydrolyzes and releases the bioactive agent. In a preferred embodiment, the bioactive agent is 2-hydroxy-4-methylthiobutanoic acid (HMTBa).

VIII. Layer Compositions Comprising a Non-Reactive Wax and a Carbonate

In another aspect, the invention provides a composition comprising a layer formed over a core, the core comprising a bioactive agent and the layer comprising non-reactive fatty acid ester and a carbonate. The core may be any core as described in section (I)(b). Suitable bioactive agents include those described in section (I)(b)(i).

The layer composition may be a mixture of a non-reactive wax and a carbonate. A non-reactive wax is a wax which does not interact appreciably with a carbonate and does not form carboxylate or fatty acid salts. In some embodiments, the non-reactive fat does not have a free carboxylic acid group. The non-reactive wax can be chosen fatty acid esters including fatty acid glycerol esters including monoglycerides, diglycerides, and triglycerides. In one preferred embodiment, the non-reactive wax is stearin. In another embodiment, the wax is hydrogenated soy or vegetable oil or a paraffin.

Carbonates may be selected from copper carbonate, zinc carbonate, calcium carbonate, magnesium carbonate, potassium carbonate, sodium carbonate, and combinations thereof. The amount of carbonate in the layer can and will vary. The amount of carbonate may range from about 1% to about 60%, or more preferably from about 15% to about 50% of the total weight of the layer. In another embodiment, the non-reactive wax is stearin and the carbonate is zinc carbonate.

Without being bound to any theory, it is thought that the non-reactive wax preserves the solubility of the carbonate so the carbonate can dissolve out of the wax matrix in some embodiments and form pores in the structure. The presence of a non-reactive wax also preserves the carbonate so that it may react with an acid external to the layer to produce $CO_2$, which promotes further fracturing of the layer. The result is a porous composition. In some embodiments, the carbonate is present in the wax in a weight to weight ratio of about 20%, 30%, 40%, 50%, or 60% or higher. In some preferred embodiments, the carbonate comprises from about 20% to about 50% of the total weight of the layer.

The layer may additionally comprise a bicarbonate. Suitable bicarbonates include alkali metal carbonates including sodium bicarbonate, potassium carbonate, calcium carbonate, magnesium carbonate, lithium carbonate and the like. When bicarbonate is present, it may be present in a ratio of about 1% to about 10% of the layer. In some preferred embodiments, potassium bicarbonate is about 2% of the total weight of the layer.

The layer may additional comprise a disintegrant or a super disintegrant. Suitable disintegrants include, without limit, starches (such as corn starch, potato starch, and the like), pregelatinized and modified starches thereof, microcrystalline cellulose, alginates, sodium starch glycolate, and gums (such as agar, guar, locust bean, karaya, pectin, and tragacanth). Non-limiting examples of suitable superdisintegrants include crospovidine, sodium carboxymethylcellulose, croscarmellose sodium, sodium starch glycolate, low substituted hydroxypropyl cellulose, and sodium bicarbonate. In one preferred embodiment, the composition may comprise sodium carboxymethylcellulose as a superdisintegrant. The disintegrant, when present, may be provided in a range of about 2% to about 20% of the total weight of the layer.

In some embodiments, the composition further comprises a reactive wax or a mixture of non-reactive and reactive waxes such as vegetable oil, cottonseed oil, or canola oil.

The layer comprising the non-reactive wax and carbonate is stable in an aqueous solution under approximately neutral pH. For example, the layer is stable at a pH level of about 6.0, about 6.5, about 7.0, and about 7.5. The layer hydrolyzes in an aqueous solution having a pH of less than about pH 5.0. Hydrolysis of the layer facilitates release of the bioactive agent.

In embodiments in which the subject is a ruminant, therefore, the layer remains stable and is not degraded during the time in which the composition is in the rumen of the subject. Upon entry into abomasum, in which the pH is low, the layer hydrolyzes and releases the bioactive agent.

In addition to a layer composition, the carbonate and wax may be formed into an agglomerated composition as described in section (II). The carbonate and wax described herein may comprise the matrix to which a plurality of bioactives are embedded.

DEFINITIONS

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The term "crystalline polymer" as used herein refers to a polymer having the characteristic or regular three-dimensional packing.

The term "enrichment" means an amount above the statistical distribution if all chiral centers had an equal probability of being alpha or beta.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "epoxy" or "epoxide" as used herein means a cyclic ether. The ring structure generally comprises from 2 to 5 carbon atoms in the ring.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "polymer" as used herein, means a molecule composed of repeating units. Polymer may refer to a homopolymer, i.e., a molecule comprising single repeat unit, or a copolymer, i.e., containing more than one repeat unit. Copolymers may be random or block. Polymer is used interchangeably with oligomer.

The term "protecting group" as used herein denotes a group capable of protecting a particular moiety, wherein the protecting group may be removed, subsequent to the reaction for which the protection is employed, without disturbing the remainder of the molecule. A variety of protecting groups and the synthesis thereof may be found in "Protective Groups in Organic Synthesis" by T. W. Greene and P. G. M. Wuts, John Wiley & Sons, 1999.

The term "semi-crystalline polymer" as used herein refers to a polymer with regions that are "crystalline" as describe above, and regions that are amorphous, having no regular packing to the three-dimensional structure.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The term "wax" as used herein can identify an oil, fatty acid, or a fatty acid ester without limitation. The term "wax" as used herein refers to both compositions that are solid at room temperature and those that are liquid at room temperature.

Having described the invention in detail, it will be apparent that modifications and variations are possible without departing from the scope of the invention defined in the appended claims.

EXAMPLES

The following examples are included to illustrate, but not to limit the claimed compositions and processes for delivering bioactive agents.

Example 1

Preparation of Coated Particles and In Vitro Release

A source of methionine was coated to protect it from degradation by bacteria but allow full absorption in the abomasum. For this, particles of the calcium salt HMTBa (MHA®; Novus International) were coated with a first coat comprising the HMTBa oligomer and a second coat comprising a hydrophobic material.

The first coat was either applied manually using a blender (neat material) or via a fluid bed coating process (i.e., Wurster coating). For the manual method, the HMTBa oligomer (O) was mixed with a polymer, such as ethyl cellulose (EC), and blended with the methionine source. For the Wurster method, the HMTBa oligomer was mixed with the polymer or dissolved in a polar organic solvent, and sprayed on the methionine source. In either method, a flow agent, such as talc (T), calcium stearate (CaSt), or $CaCO_3$ can be added to reduce tackiness. Typically, the HMTBa oligomer had a low content of monomer (e.g., 4% monomer). Table 1 details the parameters of the first coat of each particle prototype.

TABLE 1

Composition of Prototype Coated Particles - First Coat*

| Prototype # | Oligomer | Ethyl Cellulose | Talc | Calcium Stearate | CaCO$_3$ | Coat Level |
|---|---|---|---|---|---|---|
| 1 | 17% | — | 11% | — | — | manual |
| 2 | 30% | 70% | — | — | — | 22% |
| 3 | 30% | 70% | — | — | — | 5% |
| 4 | 30% | 70% | — | — | — | 10% |
| 5 | 12.3% | — | — | — | 17.5% | manual |
| 6 | 12.3 | — | — | 11% | — | manual |
| 7 | 12.3 | — | — | 11% | — | manual |

*components presented as % of total

The second coat was applied to the oligomer-coated particles via a hot melt or a fluid bed coating process. The hydrophobic material of the second coat comprised stearic acid (SA) and hydrogenated soybean oil (e.g., Dritex S (DS)). In some cases, the second coat also contained the HMTBa oligomer, EC, and/or CaCO$_3$. Table 2 details the parameters of the second coat of each particle prototype.

TABLE 2

Composition of Prototype Coated Particles - Second Coat

| Prototype # | Stearic Acid* | Dritex S* | Oligomer* | EC* | CaCO$_3$ | Coat Level (%) | Total HMTBa Load (core & coat) |
|---|---|---|---|---|---|---|---|
| 1 | 1 | 1 | — | — | — | 25 | 57% |
| 2 | 4 | 4 | 1 | 1 | — | 20 | 54% |
| 3 | 1 | 2 | — | — | — | 25 | 61% |
| 4 | 1 | 2 | — | — | — | 25 | 59% |
| 5 | 1 | 2 | — | — | 10% of coat | 25 | 50% |
| 6 | 1 | 2 | — | — | 10% of coat | 10 | 68% |
| 7 | 1 | 2 | — | — | 10% of coat | 25 | 55% |

*components presented as a ratio

The in vitro release of HMTBa was measured at different pH levels after the coated particles were incubated in pH 6.5 buffer solution for 16 hours (to mimic the typical ruminal transit time). For the release studies, the coated particles were added to pH 2.5 or pH 6.5 buffer solutions. The solutions were shaken at for 24 hours. Samples were removed at 0, 2, 4, 6, 8, and 24 hours and analyzed by HPLC.

Prototype 1. MHA® particles were manually coated with a first coat comprising HMTBa oligomer (17% of total) and talc (11% of total). The oligomer-coated particles were fluid bed coated with a 1:1 mixture of stearic acid and hydrogenated soybean oil to a coat level of 25%. The final load of HMTBa and HMTBa oligomer was 57%. The differential release profile is shown in FIG. 1A. There was substantially more release at pH 2.5 than at pH 6.5. At 24 hours, about 75% of the total HMTBa was released at pH 2.5, but less than 20% of the HMTBa was released at pH 6.5.

Prototype 2. MHA® particles were coated with a first coat comprising a thin film of ethyl cellulose and oligomer. The thin film was applied by fluid bed coating; i.e., 30% oligomer (6.7% monomer) and 70% EC were dissolved in 1:1 acetone:ethanol and sprayed onto the MHA® particles. The coating step comprised spraying 12.2% solids (i.e., O+EC) to a coat level of 22%. For the second coat, a hot melt coating of stearic acid, hydrogenated soybean oil, HMTBa oligomer, and ethyl cellulose (4:4:1:1) was used to coat the oligomer-coated particles to a 20% wax coat level. The final load of HMTBa (core and coat) was 54%. The release profile is presented in FIG. 1B; the particles displayed pH dependent release (i.e., release at pH 2.5, but not at pH 6.5). The amount released was low because these particles had a high degree of protection at low pH.

Figure 1C:
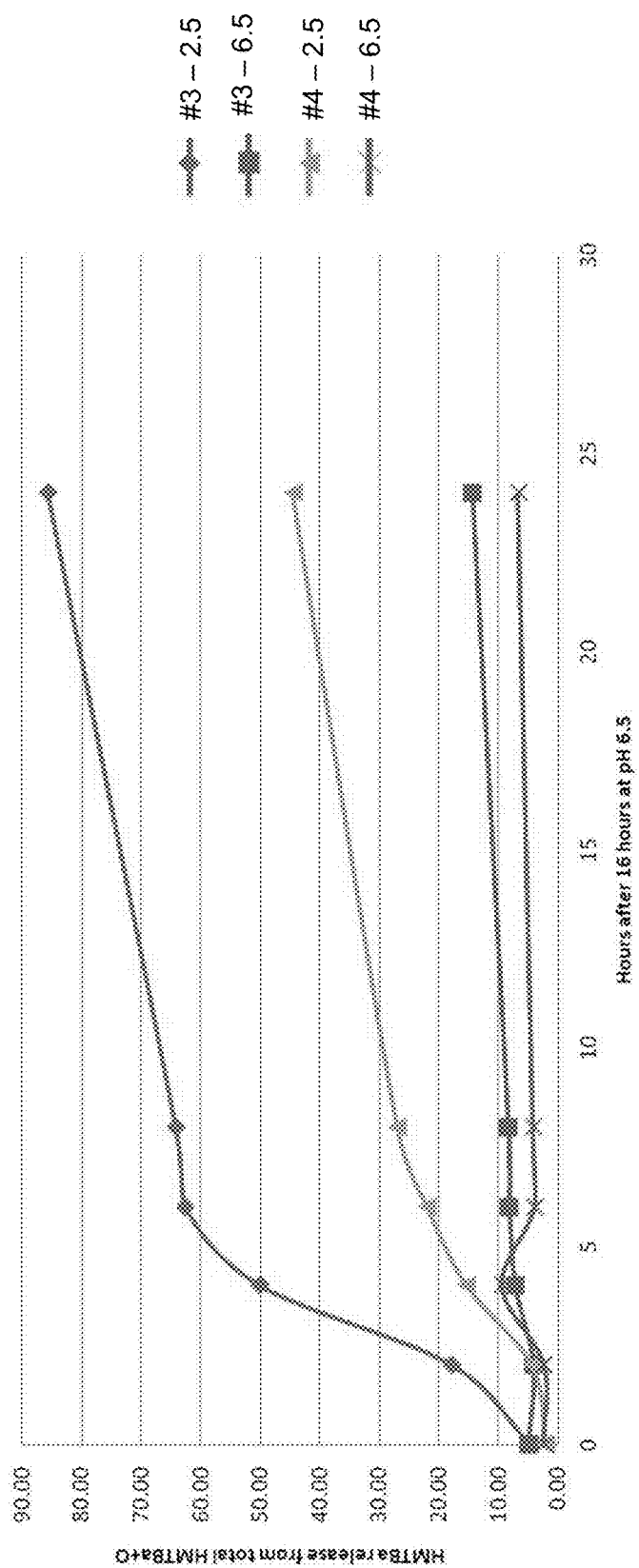

Prototypes 3 and 4. MHA® particles were coated with a first coat comprising a thin film of oligomer and ethyl cellulose. The coating was applied by fluid bed coating; i.e., 30% O and 70% EC were dissolved in 1:1 acetone:ethanol and the particles were coated to a level of 5% for prototype 3 or a coat level of 10% for prototype 4. Each population of oligomer-coated particles was then coated with a second coat comprising a 2:1 mixture of hydrogenated soybean oil and stearic acid to a coat level of 25%. The final load of HMTBa (core and coat) was 61% and 59% for prototypes 3 and 4, respectively. As shown in FIG. 1C, prototype 3 had better release at pH 2.5 than prototype 4 (i.e., 85% vs. about 45%, respectively). Neither prototype had significant release at pH 6.5.

Figure 1D:
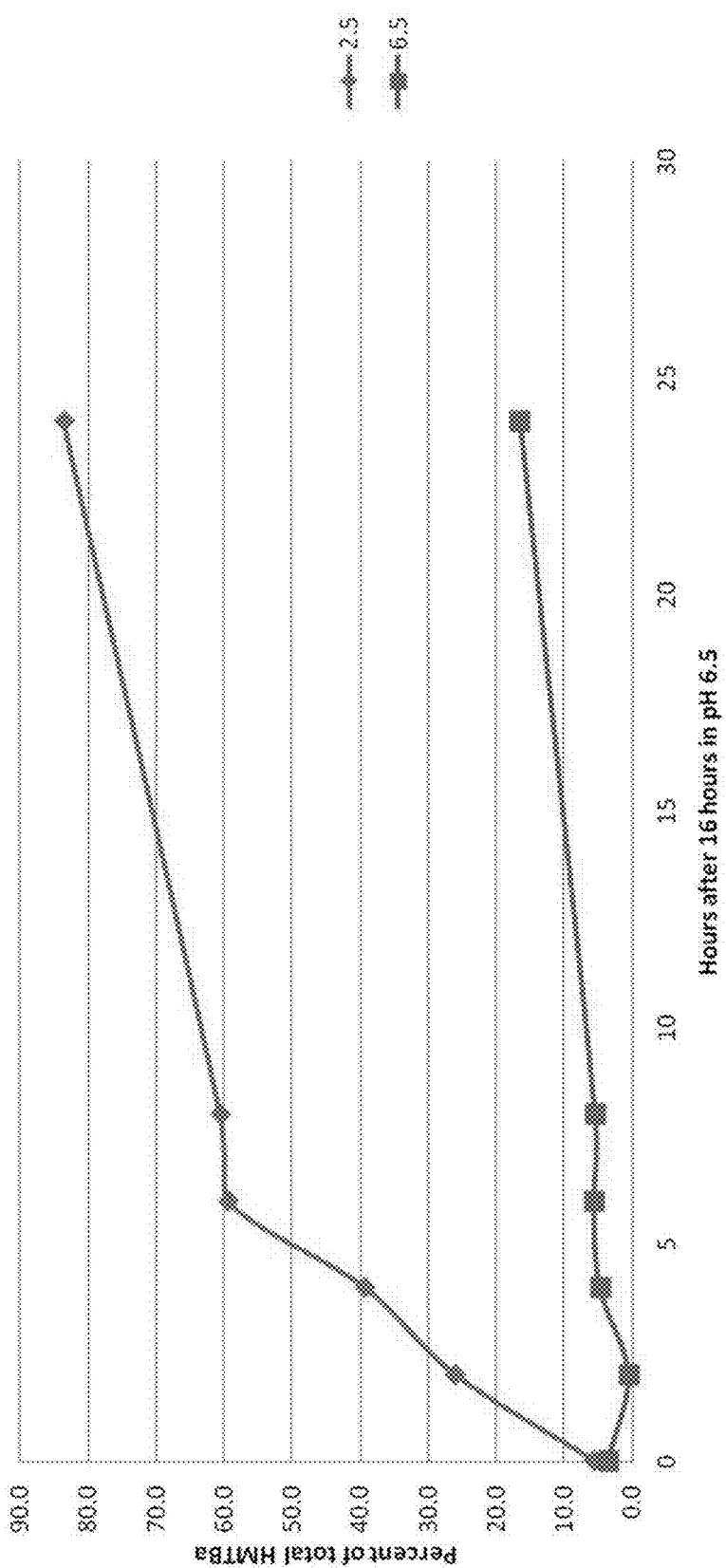
Figure 1E:
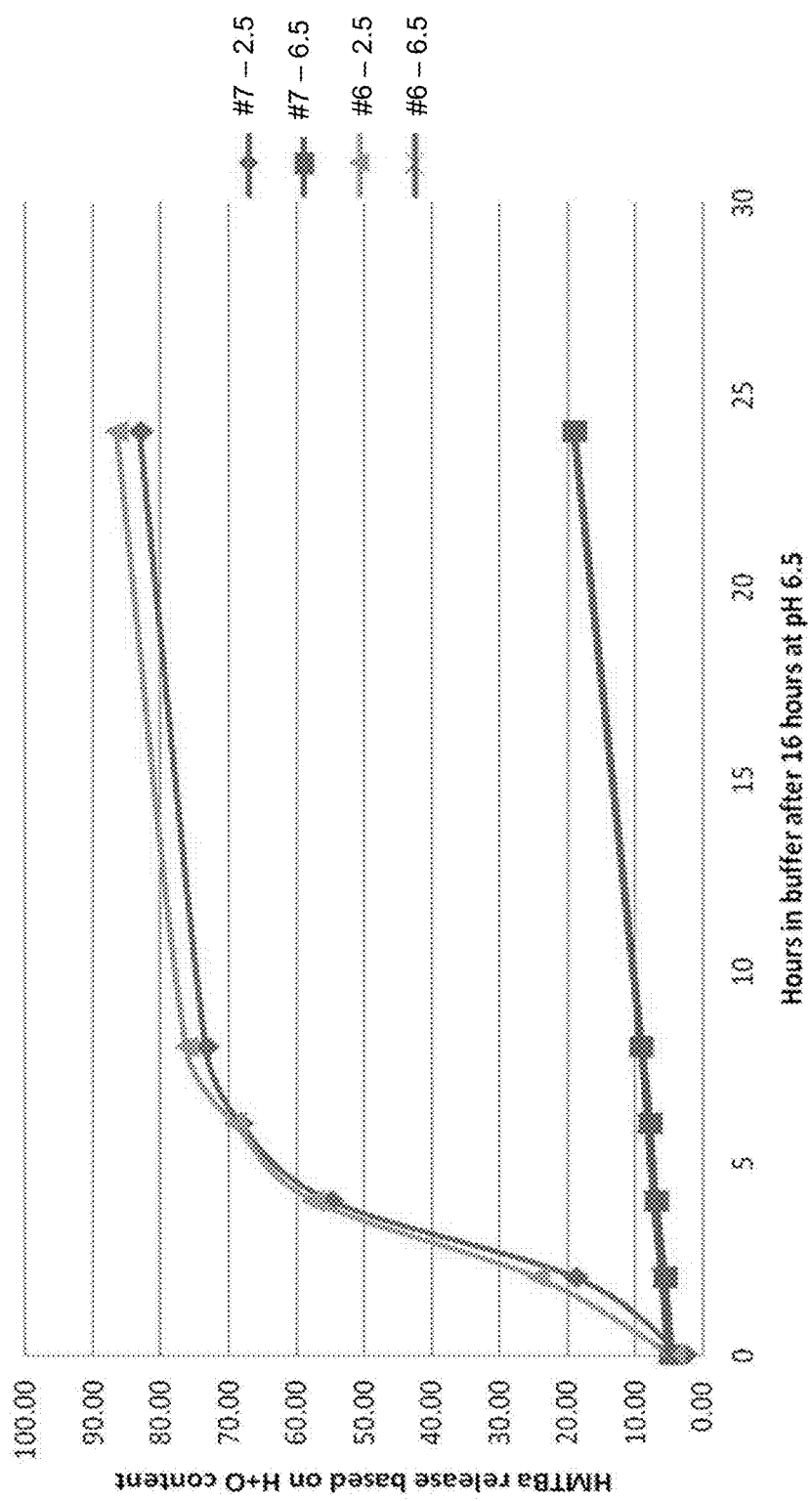

Prototype 5. Core MHA® particles were manually coated with a first coat comprising oligomer (12.3% of total) and CaCO$_3$ (17.5% of total). For the second coat, the oligomer-coated particles were fluid bed coated with a 2:1 mixture of hydrogenated soybean oil and stearic acid containing CaCO$_3$ (10% of coat) to a coat level of 15%. The total load of HMTBa (core and coat) was 50%. As shown in FIG. 1D, release was greater at pH 2.5 than pH 6.5 (e.g., 85% vs. 15% at 24 hours, respectively). Additionally, there was a high rate of release at pH 2.5 during the first 6 hours, which then decreased to a lower rate.

Prototypes 6 and 7. MHA® particles were manually coated with a first coat comprising HMTBa oligomer (12.3% of total) and 11% Ca stearate (11% of total). For the second coat, the oligomer-coated particles were fluid bed coated with a 2:1 mixture of hydrogenated soybean oil and stearic acid containing CaCO$_3$ (10% of coating) to a level of 10% for prototype 6 or a coat level of 25% for prototype 7. The total load of HMTBa (core and coat) for each of these was 68% and 55%, respectively. Prototypes 6 and 7 had similar release profiles at pH 2.5 (and both had very limited release at pH 6.5) (see FIG. 1E).

Example 2

In Situ Degradability of Coated Particles

Rumen stability is a necessary requirement for products to provide methionine activity to the tissues for protein synthesis. Escape values of >90% are considered sufficient for a rumen protected methionine source to provide substantial methionine activity when the methionine source is protected by physical means.

The seven prototype coated MHA® particles prepared in Example 1 were evaluated for their in situ degradability characteristics. Rumen cannulated steers were used to evaluate the rate and extent of rumen degradation of the prototypes as well as a reference formulation (i.e., methionine granules coated with an amino-type polymer).

Three rumen cannulated steers [BW=606±4 kg] were fed a common diet based on chopped alfalfa hay and ground corn for ad libitum consumption with an additional allotment of wheat straw for the 7 days of the experiment. Steers were weighed on day 2 and 5 of the experiment and feed offered and refused was recorded daily. Realized dry matter intake for the experimental period was 9.53 kg or 1.57% of body weight. Eight treatments (i.e., prototypes 1-7 and reference formulation control) were incubated in triplicate in each of the 3 steers for 48, 24, 6, and 0 (15 minutes in the rumen to estimate solubility) hours. In situ bags (pore size ~50 µm; 5 cm×10 cm) were preweighed and 1 g of sample was added to each bag and sealed with a zip-tie yielding approximately the recommended 10 mg ingredient/cm$^2$ of bag surface area. Bags were suspended in a mesh laundry bag, inserted in reverse order, withdrawn simultaneously, hand washed in cold water until the wash water was clear, and dried at 55° C. Dried bags with treatment were weighed and % dry matter lost was calculated.

Data were analyzed using the mixed procedure of SAS wherein sources of variation associated with steer, time of incubation, treatment and the interaction between treatment and time were included. Differences considered significant were P<0.05.

Figure 2A:
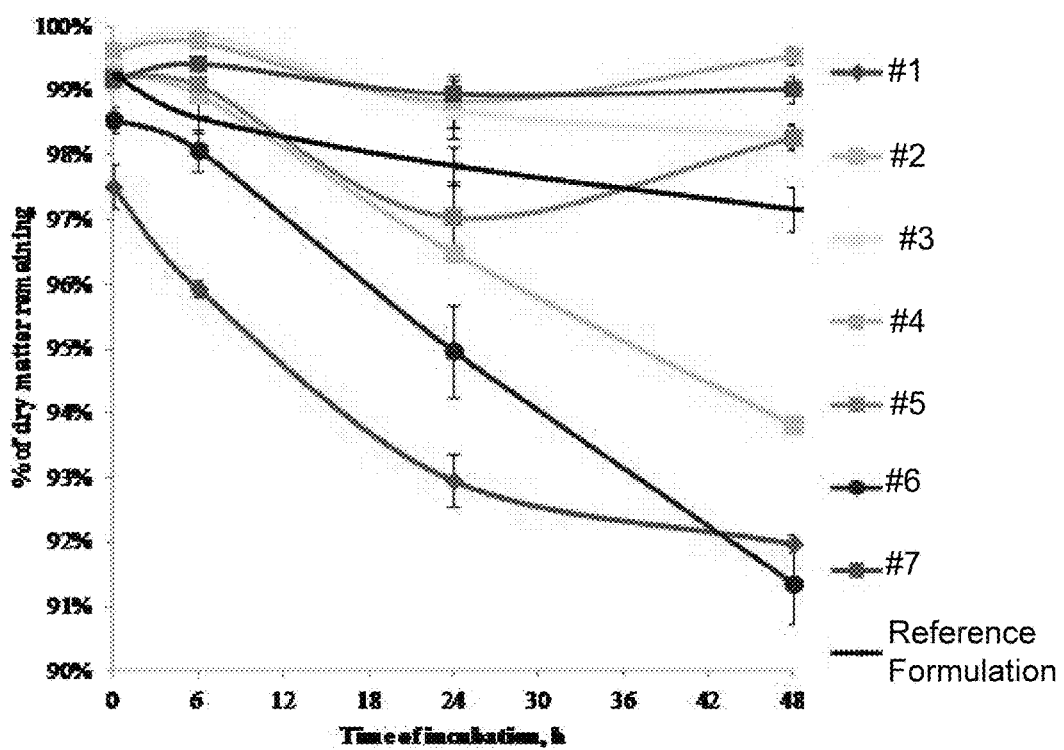
FIGS. 2A-B illustrate in situ degradation of the coated particles whose compositions are described in Tables 1 and 2.
Figure 2B:
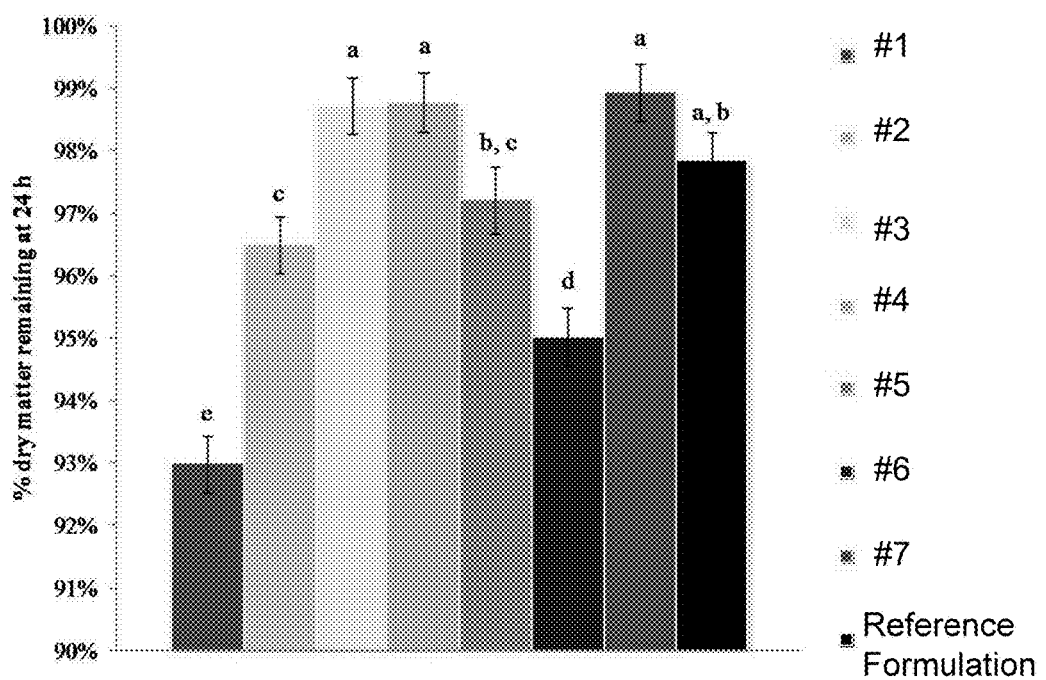

Degradation profiles for the prototype protected MHA® particles and reference formulation are shown in FIG. 2A. All treatments tested had >90% of dry matter remaining after 48 hours in the rumen. The products differed in the degree to which they were protected, i.e., some of the prototypes had relatively constant rates of release (e.g., prototype #6) and some of the prototypes had extremely low levels of release within the rumen (e.g., prototypes #4 and #7). Typical retention time within the rumen is between 12 and 20 hours for the particle phase of rumen digesta. FIG. 2B shows the percent of dry matter remaining for the different prototypes and the reference formulation after incubation in the rumen for 24 h. Retention time within the rumen is determined by a number of factors including: specific gravity, particle size, susceptibility to degradation, and the intake of the cow. Results of this experiment are relevant to the susceptibility to degradation, and by this metric all of the prototypes are considered to be quite resistant to rumen degradation. The order of resistance is presented in Table 3 (based on 24 hour data where 1 is most resistant).

TABLE 3

In Situ Resistance to Degradation.

| Sample | 1$^{st}$ coat | 2$^{nd}$ coat | Rank |
|---|---|---|---|
| Prototype 1 | O/T - manual | SA/DS - 25% | 8 |
| Prototype 2 | O/EC - thin film 22% | SA/DA/O/EC - 30% | 6 |
| Prototype 3 | O/EC - thin film 5% | SA/DS - 25% | 3 |
| Prototype 4 | O/EC - thin film 10% | SA/DS - 25% | 2 |
| Prototype 5 | O/CaCO$_3$ - manual | SA/DS/CaCO$_3$ - 25% | 5 |
| Prototype 6 | O/CaSt - manual | SA/DS/CaCO$_3$ - 10% | 7 |
| Prototype 7 | O/CaSt - manual | SA/DS/CaCO$_3$ - 25% | 1 |
| Reference Formulation | Amino-type polymer coating | | 4 |

Example 3

Preparation of Agglomerated Composition

Figure 3:
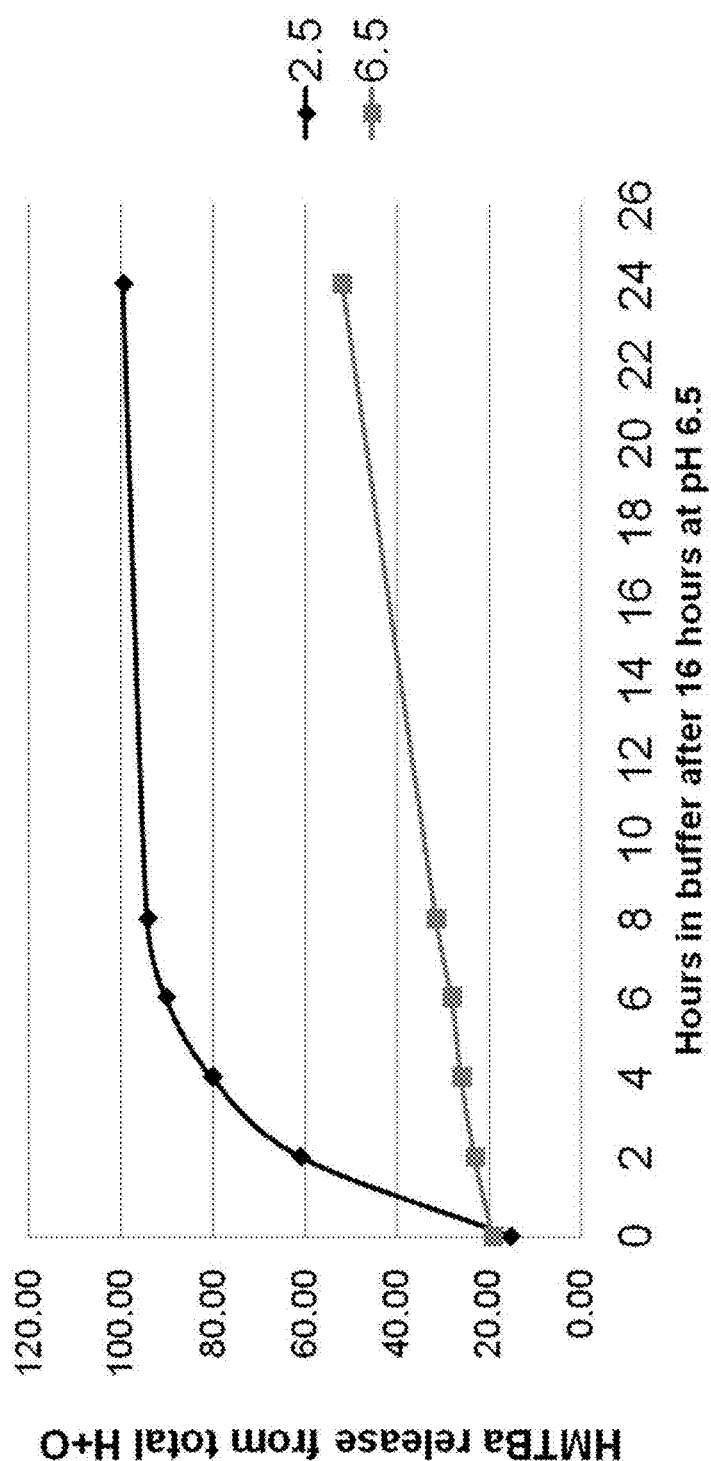
FIG. 3 shows in vitro release of HMTBa at pH 2.5 and 6.5 from an agglomerated matrix preparation.
Figure 4:
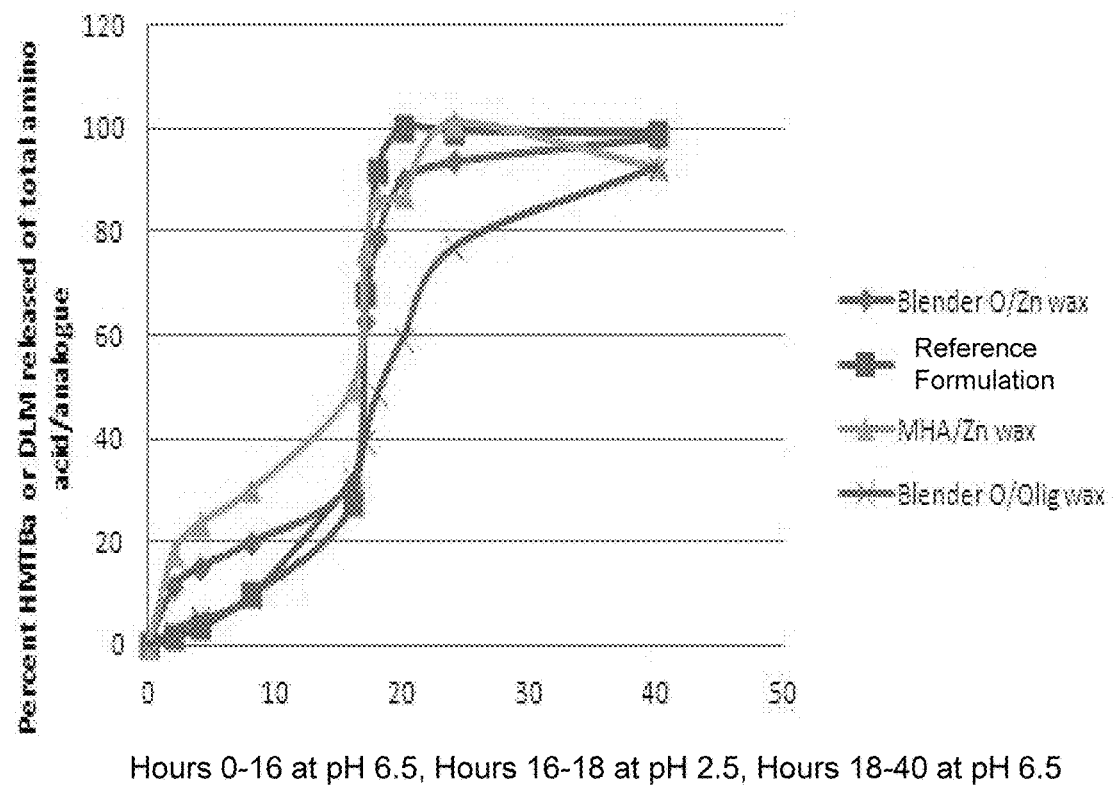
FIG. 4 presents in vitro release of HMTBa from the indicated formulations as a function of pH and time. Samples were incubated at pH 6.5 from time 0 to hour 16, pH 2.5 from hour 16 to hour 18, and pH 6.5 from hour 18 to hour 40.

The following example was designed to determine whether agglomerated matrix compositions would provide pH dependent release. MHA® powder was granulated with ethyl cellulose and HMTBa oligomer at 30% oligomer using 15% solids. The powder was coated to 23% to a total load of HMTBa of 50%. The granulated mixture was fluid bed coated with a 1:1 mixture of hydrogenated soybean oil and stearic acid to a coat level of 25%. The release of HMTBa was measured at pH 2.5 or pH 6.5 after 16 hours at pH 6.5 essentially as detailed above in Example 1. As shown in FIG. 3, the agglomerated composition displayed release in pH 2.5 buffer.

Example 4

Coated Particles Comprising Metal Carbonate

To determine whether a hydrophobic coating comprising a metal carbonate would provide pH dependent release, the following coated particles were prepared. "Blender O/Zn wax" particles were prepared by blender coating MHA® particles with HMTBa oligomer (i.e., 7.5% or 12.4% oligomer, with a total HMTBa load of 60-70%) and then over-coating the particles with a 1:1 mixture of stearic acid and hydrogenated soybean oil containing 30-40% Zn or Ca carbonate and 2-10% croscarmellose to a coat level of 15, 20, or 25%. "Blender O/Oligo wax" particles were prepared by blender coating MHA® particles with HMTBa oligomer (i.e., 7.5% or 12.4% oligomer, with a total HMTBa load of 60-70%) and then over-coating them with a 1:1 mixture of stearic acid and hydrogenated soybean oil containing 10-60% oligomer (and optionally, methyl cellulose or croscarmellose) to a coat level of 15, 20, or 25%. "MHA®/Zn wax" particles were prepared by coating MHA® particles with 1:1 mixture of stearic acid and hydrogenated soybean oil containing 30-40% Zn or Ca carbonate and 2-10% croscarmellose to a coat level of 15, 20, or 25%.

To measure in vitro release, samples were incubated at pH 6.5 from time 0 to hour 16 (i.e., rumen phase), pH 2.5 from hour 16 to hour 18 (i.e., abomasum phase), and pH 6.5 from hour 18 to hour 40 (i.e., intestine phase). Aliquots were removed from each sample at predetermined times and analyzed by HPLC. The release of the amino acid from all preparations increased dramatically when the pH was lowered (see FIG. 4). Some preparations (e.g., Blender O/Zn wax and Blender O/Oligo wax) exhibited slow rates of release at pH 6.5.

Example 5

Coated Particles Comprising Wax Overcoat

MHA® particles were coated with oligomer (as detailed above in Examples 1 and 3) and over-coated with either of two "wax" coatings. The two coatings were a "Zn wax" coat or an "oligomer wax" coat, which are detailed below in Tables 4 and 5, respectively. The coatings were applied by fluid bed coating to coat levels of 15-25%. The wax of the Zn wax coating comprised stearin (i.e., an ester of glycerol and stearic acid; stearin may be derived from palm oil and other oils), a hydrogenated vegetable oil (e.g., soy, canola, cotton seed, corn, etc.), or combinations thereof. The wax of the Oligomer wax coated comprised stearin, hydrogenated vegetable oil, stearic acid, or combinations thereof.

TABLE 4

Zn wax formulations.

| Prototype # | Stearin | Hydrogenated Veg Oil | Zn Carbonate | Croscarmellose | Bicarbonate |
|---|---|---|---|---|---|
| 8 | 20 g | 20 g | 40 g | 10 g | 0 |
| 9 | 53 g | 0 | 40 g | 5 g | 2 g |
| 10 | 0 | 55 g | 35 g | 10 g | 0 |
| 11 | 32 g | 32 g | 31 g | 5 g | 0 |

TABLE 5

Oligomer wax formulations.

| Proto-type | Stearin | Hydrogenated Veg Oil | Stearic Acid | Ethyl Cellulose | Oligomer |
|---|---|---|---|---|---|
| 12 | 18 g | 18 g | 10 g | 2 g | 35 g |
| 13 | 0 | 15 g | 15 g | 5 g | 30 g |

Example 6

Simulated In Situ Release from Coated Particles

A series of coated MHA® particles were prepared in which the coating comprised HMTBa oligomer, stearic acid, poly-2-vinylpyridine-co-styrene (PVPS; MW~130-220K), and, optionally, ethyl cellulose and the coating level varies from 10-15%. Table 6 presents the various formulations.

TABLE 6

Coat Level and Composition of Coated Particles

| Formulation # | Coat Level (%) | Stearic Acid* | PVPS* | Ethyl Cellulose* | Oligomer* |
|---|---|---|---|---|---|
| 70418 | 15 | 77.35 | 14.83 | 0 | 4.74 |
| 70430 | 10 | 84.49 | 7.14 | 0 | 4.74 |
| 70431 | 15 | 84.49 | 7.14 | 0 | 4.74 |
| 70432 | 10 | 77.35 | 14.83 | 3.07 | 4.74 |
| 70433 | 12 | 77.35 | 14.83 | 3.07 | 4.74 |
| 70434 | 15 | 81.2 | 15.56 | 0 | 0 |
| 70435 | 10 | 84.49 | 7.14 | 3.07 | 4.74 |
| 70437 | 12 | 84.49 | 7.14 | 0 | 4.74 |
| 70438 | 12 | 77.35 | 14.83 | 0 | 4.74 |
| 70439 | 10 | 77.35 | 14.83 | 0 | 4.74 |
| 40740 | 10 | 84.49 | 7.14 | 0 | 4.74 |

*component presented as % of coating

The amount of HMTBa released from some of the formulations listed in Table 6 was tested using a gravimetric in vitro bag test. This test is a simulation of the rumen bag test described above in Example 2. For the in vitro bag test, coated particles were placed in a nylon bag which was then sealed with a zip-tie. Four separate bags were prepared for each formulation to be tested. The initial weight of each bag containing coated particles was measured. Each bag was place in a container filed with a simulated rumen fluid that was buffered to a different pH level. The containers (with the bags) were closed and placed inside a 40° C. incubator oven, with constant shaking, for a period of 18 hours.

Figure 5:
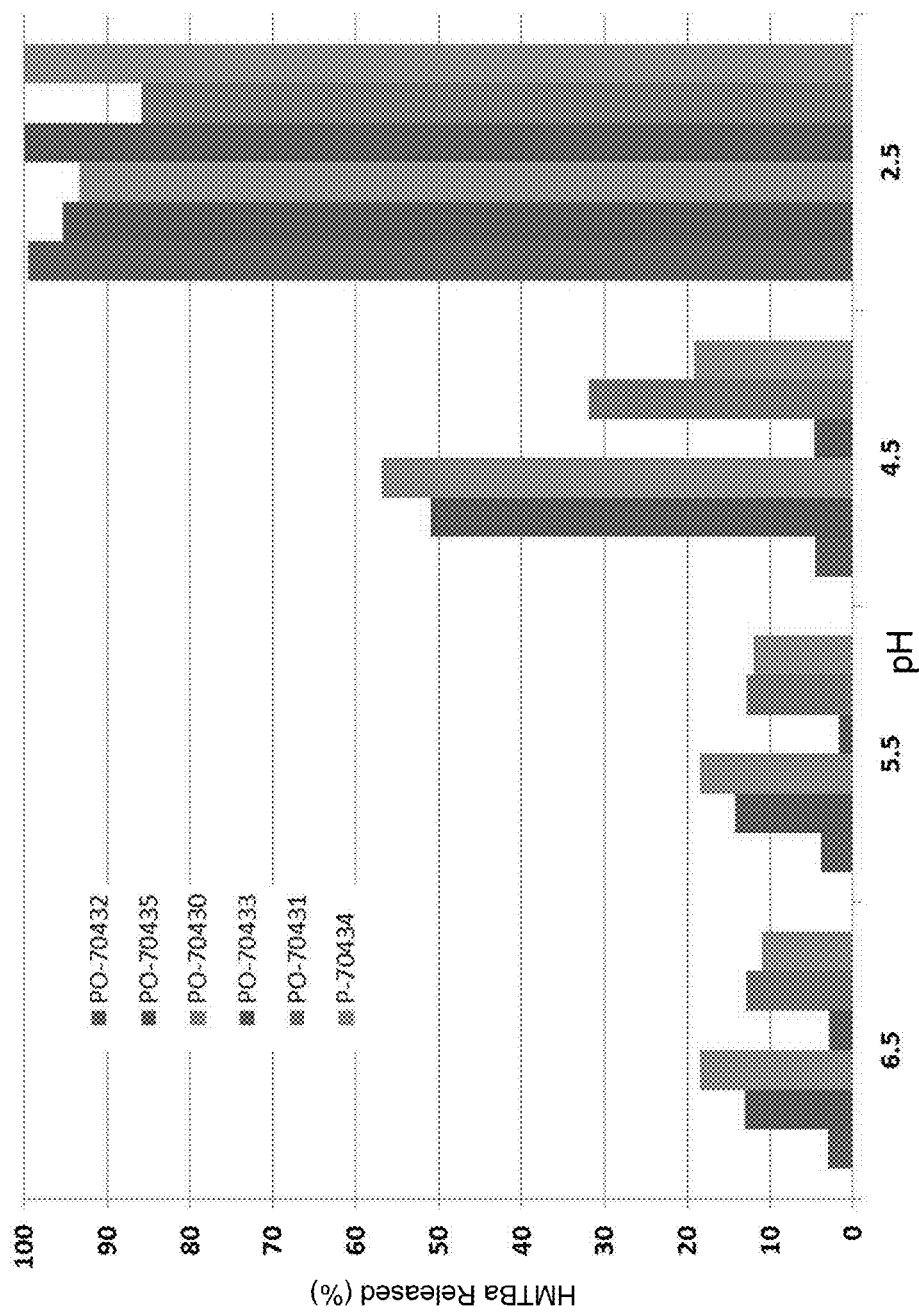
FIG. 5 documents release from coated particles in a simulated in vitro bag test. The composition of the coated particles is detailed in Table 6. Shown is the percent of HMTBa released as a function of pH.

After 18 hours, samples were removed from each container and the amount of HMTBa was measured using an HPLC method. FIG. 5 shows the percent of HMTBa released at the various pH levels during this 18 hour period. All formulations showed limited release of HMTBa at pH 6.5 and 5.5, but good release at pH 2.5.

Example 7

Time Course of In Vitro Release

Figure 6:
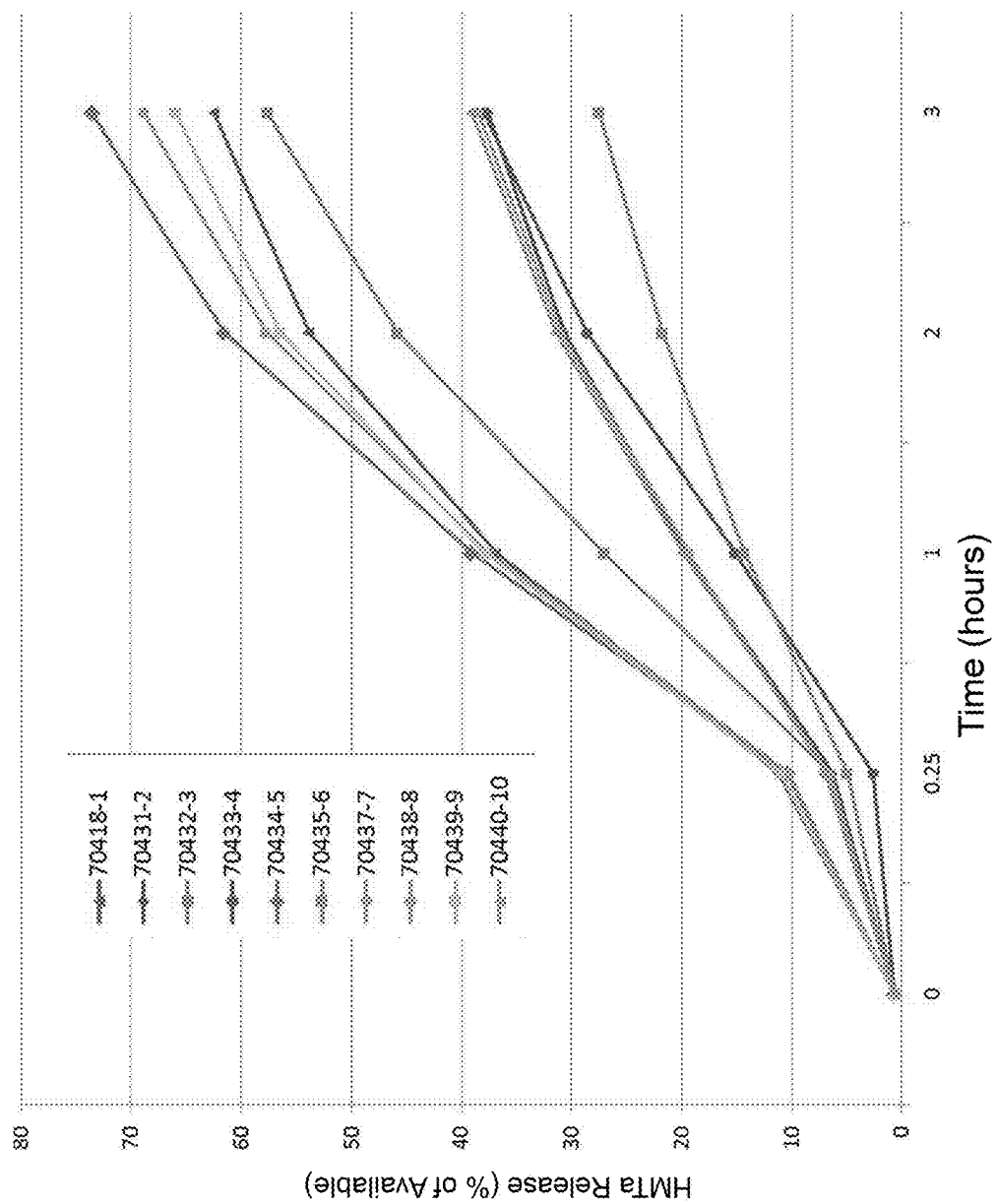
FIG. 6 presents the in vitro release kinetics at pH 2.5 of the coated particles detailed in Table 6. Shown is the percent of HMTBa released over time.

The release of HMTBa from the formulations listed in Table 6 was examined at pH 2.5. Formulations were placed in a pH 2.5 solution, incubated at 40° C. (i.e., ruminant body temperature) and samples were removed at regular intervals over a 3 hour time period. The amount of HMTBa was determined using an HPLC assay. FIG. 6 presents the kinetics of release. All formulations had a low release rate during the initial 15 minutes and then the rates of release increased.

Example 8

Physical Resilience of the Coated Particles

The ability the coated particles to withstand mastication or mechanical manipulations was tested using an impact test. For this, a 24" carbon steel pipe was fitted with end caps and a cylindrical 95 gram stainless steel weight having an outer diameter that is about the same as the inner diameter of the pipe. The bottom of the pipe was capped, a sample of the test formulation was placed in the bottom of the capped pipe, the weight was placed on top of the formulation, and the top end of the pipe was capped. The pipe was inverted so that the weight returned to what was the top of the pipe. The pipe was then brought back to starting position and the weight fell to the bottom and hit the test formulation. This was counted as 1 impact. The process was repeated a certain number of times (or weight impacts). After the pre-determined number of weight impacts was completed, the end cap was removed and the test formulation was collected, including all of the fines or powder. The recovered test formulation was mixed with a pH 5.5 solution and incubated for 2 hours at 40° C. Samples were removed and analyzed by HPLC to determine the amount of active that was released into the solution.

The compositions of the coated particles that were tested are detailed in Table 7. The reference formulation was methionine granules coated with an amino-type polymer.

TABLE 7

Coated Particle Formulations

| Formulation # | Coat Level (%) | Stearic Acid* | PVPS* | Ethyl Cellulose* | Oligomer* |
|---|---|---|---|---|---|
| 75903 | 15.5 | 77.35 | 14.83 | 3.07 | 4.74 |
| 75904 | 17 | 77.35 | 14.83 | 3.07 | 4.74 |
| 75905 | 15.25 | 77.35 | 14.83 | 3.07 | 4.74 |

*presented as % of coating

Figure 7:
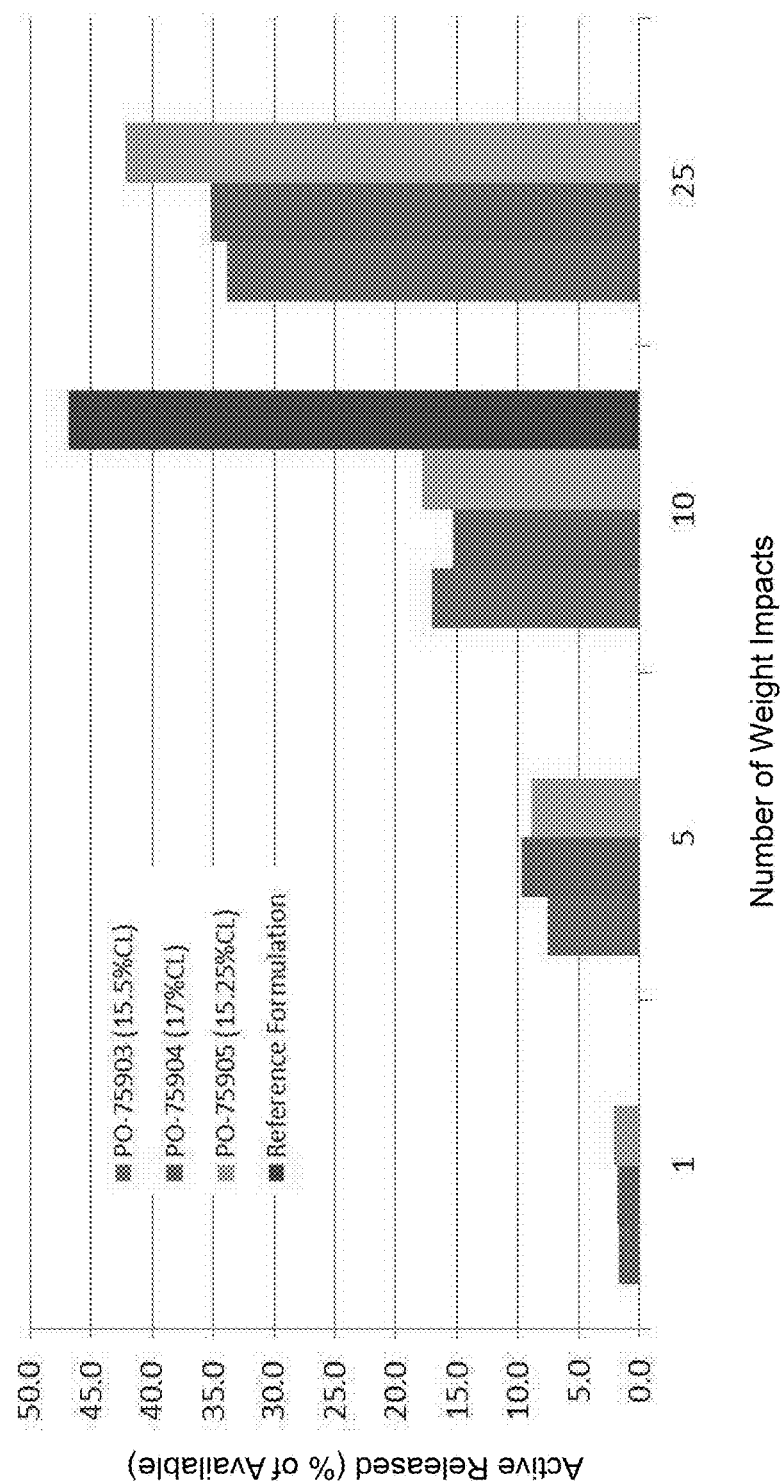
FIG. 7 shows the physical resilience of the coated particles detailed in Table 7 and a reference formulation. Plotted is the percent of HMTBa or D,L-methionine released after the indicated number of weight impacts.

The results are presented in FIG. 7. The three test formulations retained more than 50% of the active (i.e., HMTBa) even after 25 weight impacts, whereas the reference formulation lost about 50% of the active (i.e., D,L-methionine) after 10 weight impacts.

Example 9

Comparative Simulated In Situ Release and Kinetics of Release

Figure 8:
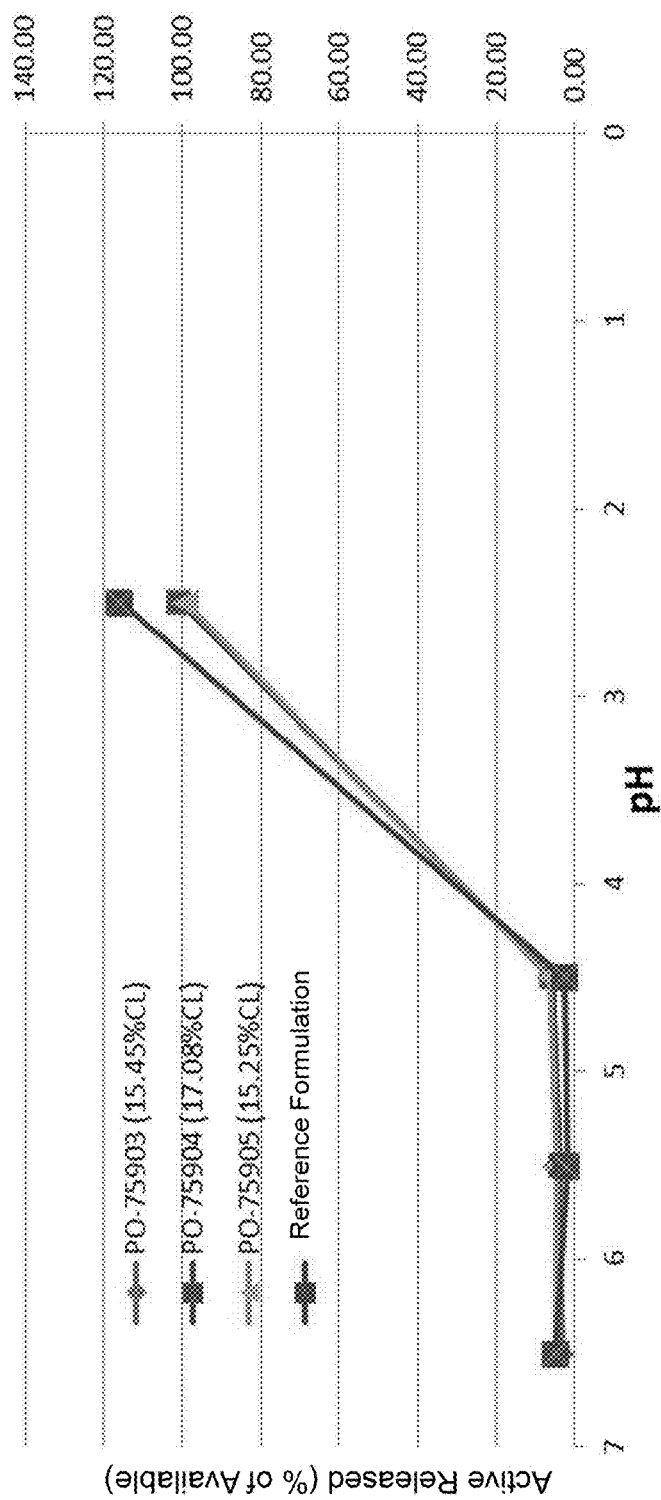
FIG. 8 presents release from the coated particles detailed in Table 7 and a reference formulation in a simulated in situ bag test. Plotted is the percent of HMTBa or D,L-methionine released as a function of pH.

The three test formulations described above in Example 8 and the reference formulation were subjected to the in vitro bag test essentially as described above in Example 6. FIG. 8 shows that all formulations displayed release at pH 2.5.

Figure 9:
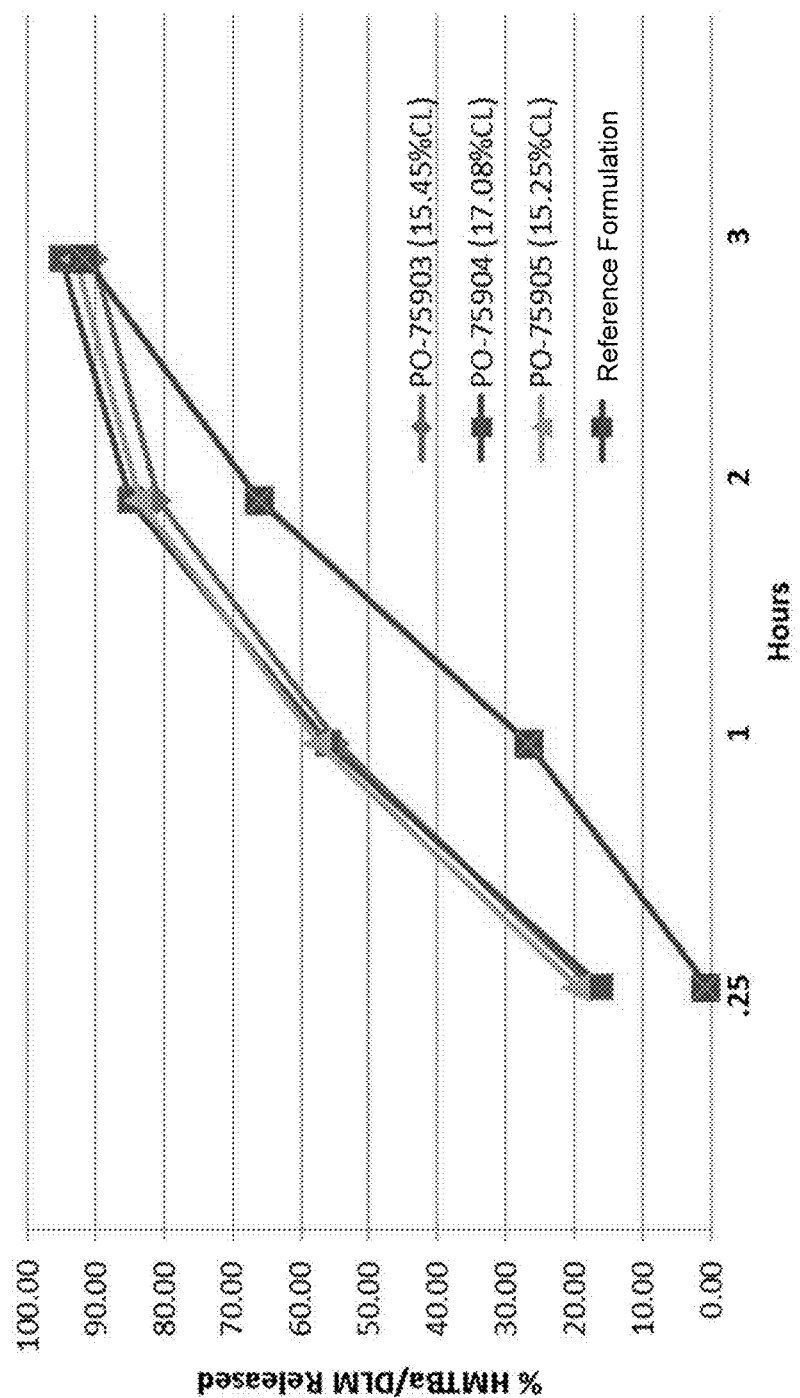
FIG. 9 shows the in vitro release kinetics at pH 2.5 of the coated particles detailed in Table 7 and a reference formulation. Shown is the percent of HMTBa or D,L-methionine released over time.

The kinetics of release was examined in the three test formulations described above in Example 8 and the reference formulation essentially as described above in Example 7. The results are shown in FIG. 9. The three test formulations had higher rates of release at the earlier time points (i.e., 30 min, 1 hr, and 2 hr) than the reference formulation.

What is claimed is:

1. A composition comprising a layer formed over a core, the core comprising a bioactive agent, the layer comprising a first polymer comprising a repeat unit of Formula (I) and at least one additional agent, the repeat unit of Formula (I) having the following structure:

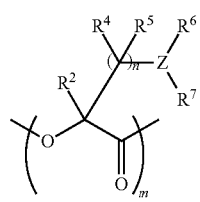

(I)

wherein:
$R^2$, $R^4$, and $R^5$ are independently hydrogen, hydrocarbyl, or substituted hydrocarbyl;
$R^6$ is hydrogen, hydrocarbyl, or substituted hydrocarbyl;
$R^7$ is optionally present, when present it is hydrogen, hydrocarbyl, or substituted hydrocarbyl;
Z is sulfur, sulfone, sulfoxide, or selenium;
n is an integer $\geq 1$; and
m is an integer $>1$; and
wherein the at least one additional agent is chosen from polymers, waxes, fatty acids, fatty acid esters, or flow agents.

2. The composition of claim 1, wherein the repeat unit of the first polymer comprises Formula (II):

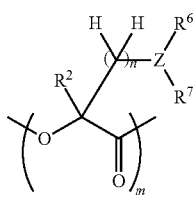

(II)

wherein $R^2$, $R^6$, $R^7$, Z, n, and m are as defined in claim 1.

3. The composition of claim 1, wherein Z is sulfur.

4. The composition of claim 1, wherein $R^6$ is methyl or ethyl.

5. The composition of claim 1, wherein $R^7$ is not present.

6. The composition of claim 1, wherein n is an integer from 1 to 5.

7. The composition of claim 1, wherein the repeat unit of the first polymer comprises Formula (III):

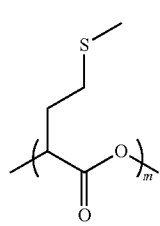

(III)

wherein m is an integer $>1$.

8. The composition of claim 1, wherein the first polymer has an average molecular weight of at least 500 Da.

9. The composition of claim 1, wherein the bioactive agent is an essential oil, an amino acid, an analogue of an amino acid, a vitamin, a mineral, an antioxidant, a pigment, an enzyme, an organic acid, a poly unsaturated fatty acid, a prebiotic, a probiotic, a herb, a pharmaceutically active agent, or a combination thereof.

10. The composition of claim 1, wherein the layer comprises 10% by weight of the composition.

11. The composition of claim 1, wherein the at least one additional agent is a second polymer.

12. The composition of claim 11, wherein the second polymer is a pH-sensitive polymer.

13. The composition of claim 1, wherein the bioactive is a calcium salt of 2-hydroxy-4-methylthiobutanoic acid.

14. The composition of claim 1, wherein the composition hydrolyzes in aqueous solution at a pH below about 5.0.

15. The composition of claim 1, wherein the composition has a substantially constant release profile at a pH below about 5.0.

16. An agglomerated composition comprising a plurality of bioactive active agents embedded in a matrix, the matrix comprising a first polymer having a repeat unit of Formula (I) and at least one additional agent, the repeat unit of Formula (I) having the following structure:

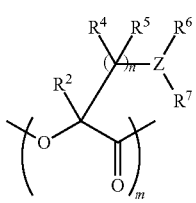

(I)

wherein:
$R^2$, $R^4$, and $R^5$ are independently hydrogen, hydrocarbyl, or substituted hydrocarbyl;
$R^6$ is hydrogen, hydrocarbyl, or substituted hydrocarbyl;
$R^7$ is optionally present, when present it is hydrogen, hydrocarbyl, or substituted hydrocarbyl;
Z is sulfur, sulfone, sulfoxide, or selenium;
n is an integer $\geq 1$; and
m is an integer $>1$; and
wherein the at least one additional agent is chosen from polymers, waxes, fatty acids, fatty acid esters, or flow agents.

17. The composition of claim 16, wherein the repeat unit of the first polymer comprises Formula (II):

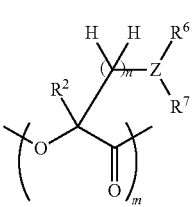

(II)

wherein $R^2$, $R^6$, $R^7$, Z, n, and m are as defined in claim 16.

18. The composition of claim 16, wherein Z is sulfur.

19. The composition of claim 16, wherein $R^6$ is methyl or ethyl.

20. The composition of claim 16, wherein $R^7$ is not present.

21. The composition of claim 16, wherein the repeat unit of the first polymer comprises Formula (III):

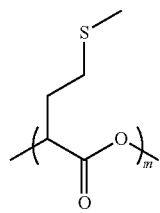

(III)

wherein m is an integer >1.

22. The composition of claim 16, wherein the bioactive agent is an essential oil, an amino acid, an analogue of an amino acid, a vitamin, a mineral, an antioxidant, a pigment, an enzyme, an organic acid, a poly unsaturated fatty acid, a prebiotic, a probiotic, a herb, a pharmaceutically active agent, or a combination thereof.

23. The composition of claim 16, wherein the at least one additional agent is a second polymer.

24. The composition of claim 16, wherein the composition further comprises at least one layer formed over the matrix.

25. The composition of claim 16, wherein the bioactive is a calcium salt of 2-hydroxy-4-methylthiobutanoic acid.

26. The composition of claim 16, wherein the composition hydrolyzes in aqueous solution at a pH below about 5.0.

27. The composition of claim 16, wherein the composition has a substantially constant release profile at a pH below about 5.0.

28. A food source comprising a nutritive source and the composition recited in claim 1.

29. A method for providing a bioactive agent to a subject, the method comprising administering the composition as recited in claim 1 to the subject.

30. The method of claim 29, wherein the subject is a ruminant and the bioactive agent is released after passage of the composition through the rumen.

* * * * *